(12) United States Patent
Gmeiner et al.

(10) Patent No.: US 8,586,603 B2
(45) Date of Patent: Nov. 19, 2013

(54) AMINOTETRALINE DERIVATIVES

(76) Inventors: Peter Gmeiner, Erlangen-Buckendorf (DE); Miriam Ruberg, Neustadt (DE); Harald Hüebner, Heroldsbach (DE)

( * ) Notice: Subject to any disclaimer, the term of this patent is extended or adjusted under 35 U.S.C. 154(b) by 0 days.

(21) Appl. No.: 13/517,337

(22) PCT Filed: Dec. 20, 2010

(86) PCT No.: PCT/EP2010/070194
§ 371 (c)(1), (2), (4) Date: Jul. 9, 2012

(87) PCT Pub. No.: WO2011/076708
PCT Pub. Date: Jun. 30, 2011

(65) Prior Publication Data
US 2012/0277262 A1   Nov. 1, 2012

(30) Foreign Application Priority Data

Dec. 22, 2009   (EP) ..................................... 09015827

(51) Int. Cl.
| | | |
|---|---|---|
| A61K 31/437 | (2006.01) | |
| A61K 31/381 | (2006.01) | |
| A61K 31/165 | (2006.01) | |
| C07D 471/04 | (2006.01) | |
| C07D 333/24 | (2006.01) | |
| C07D 333/56 | (2006.01) | |
| C07C 217/74 | (2006.01) | |
| C07C 233/23 | (2006.01) | |

(52) U.S. Cl.
USPC ........... 514/300; 514/438; 514/443; 514/617; 514/643; 546/121; 549/58; 549/77; 564/182; 564/287

(58) Field of Classification Search
USPC ........ 549/74, 77, 58; 514/438, 300, 643, 617, 514/443; 564/287, 182; 546/121
See application file for complete search history.

(56) References Cited

U.S. PATENT DOCUMENTS

| | | |
|---|---|---|
| 6,884,434 B1 | 4/2005 | Muller et al. |
| 7,244,846 B2 | 7/2007 | Dorsch et al. |
| 7,351,732 B2 | 4/2008 | Del Rio Zambrana et al. |
| 7,479,559 B2 | 1/2009 | Brodney et al. |
| 7,547,700 B2 | 6/2009 | Vacher et al. |
| 7,816,394 B2 | 10/2010 | Yoneto et al. |
| 2005/0032873 A1 | 2/2005 | Hatzenbuhler et al. |
| 2010/0189793 A1 | 7/2010 | Meyer et al. |

FOREIGN PATENT DOCUMENTS

| | | |
|---|---|---|
| EP | 0385658 | 9/1990 |
| WO | 8103491 A1 | 12/1981 |
| WO | 9965887 | 12/1999 |
| WO | 0147503 | 7/2001 |
| WO | 02060423 | 8/2002 |
| WO | 2009060030 | 5/2009 |

OTHER PUBLICATIONS

Vippagunta et al., Crystalline solids, 2001, Advanced Drug Delivery Reviews, 48, pp. 3 and 18.*
Naiman N et al: "2-(Alkylamino) Derivatives: Interaction With 5-HT1A Serotonin Binding", Journal of Medicinal Chemistry, American Chemical Society, vol. 32, No. 1, Jan. 1, 1989; pp. 253-256.
Jonathan Savitz: Progress in Neurobiology: 5-HT1A receptor function in major depressive disorder; Progress in Neurobiology 88 (2009) 17-31.
Lars-Erik Arvidsson: 8-Hydroxy-2-(di-n-p. ropylamino)tetralin, a New Centrally Acting 5-Hydroxytryptamine Receptor Agonist; J. Med. Chem. 1981, 24, 921-923.
Lars-Erik Arvidsson: 8-Hydroxy-2-(alkylamino)tetralins and Related Compounds as Central 5-Hydroxytryptamine Receptor Agonists; J. Med. Chem. 1984, 27,45-51.
J. P. Mason: Pharmacokinetics of the 5-hydroxytryptanninel~agonist 8-hydroxy-2-(N,N-di-rz-propylamino)tetralin (8-OHDPAT) in the rat after intravenous and oral administration; XENOBIOTICA, 1995, vol. 25, No. 12, 1371-1380.
F. Lejeune et al: Interactions of (1)- and (2)-8- and 7-Hydroxy-2-(Di-n-Propylamino)tetralin at Human (h)D3, hD2 and h Serotonin1A Receptors and Their Modulation of the Activity of Serotoninergic and Dopaminergic Neurones in Rats; The Journal of Pharmacology and Experimental Therapeutics vol. 280, No. 3; 1241-1249, 1997.
Lo Hansson et al: Quantitative structure-activity relationships in the 8-amino-6,7,8,9-tetrahydro-3H-benz[e]indole ring system. Analysis of serotonin 5-HT1A, effects in vivo and in vitro via partial least squares regression; Eur J Med Chem (1997) 32, 571-582.

(Continued)

*Primary Examiner* — Kristin Vajda
(74) *Attorney, Agent, or Firm* — Schmeiser, Olsen & Watts LLP

(57) ABSTRACT

The present application relates to compounds of formula (I): and pharmaceutically acceptable salts and solvates thereof, wherein the substituents are as defined herein, compositions containing such compounds and the uses of such compounds in producing medicaments for the treatment of various diseases and conditions, such as of the central nervous system.

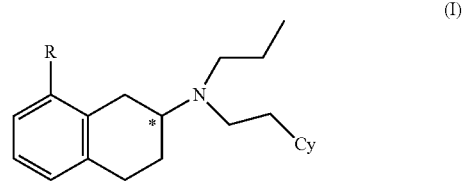

(I)

16 Claims, 3 Drawing Sheets

(56) References Cited

OTHER PUBLICATIONS

Michael D. Ennis et al: Structure-Activity Relationships in the 8-Amino-6,7,8,9-tetrahydro-3H-benz[e]indoRlien g System. 2. Effect of 8-Amino Nitrogen Substitution on Serotonin Receptor Binding and Pharmacology; J. Med. Chem. 1995,38, 2217-2230.

Peter Stjernloef et al: (S)- and (R)-8-(Di-n-propylamino)-6,7,8,9-tetrahydro-3~-benz[e]indole- 1-carbaldehyde: A New Class of Orally Active 5-HTI1A-Receptor Agonists; J. Med. Chem. 1993,36, 2059-2065.

Philip W. Miller et al: Synthesis of 11C, 18F, 15O, and 13N Radiolabels for Positron Emission Tomography; Angew. Chem. Int. Ed. 2008, 47, 8998-9033.

Subbu Venkatraman et al: Skin adhesives and skin adhesion 1. Transdermal drug delivery systems; Biomaterials 19 (1998) 1119-1136.

Mark R Prausnitz et al: Transdermal drug delivery; nature biotechnology vol. 26 No. 11 Nov. 2008, 1261-1268.

Katsuya Awano et al: Synthesis of Metobolites and related compounds of 3-isobutyryl-2-isopropylpyrazolo; Chem. Pharm. Bull. 40 (3), 631-638 1992.

Stefan Loeber et al: Fused Azaindole Derivatives: Molecular Design, Synthesis and In Vitro Pharmacology Leading to the Preferential Dopamine D3Receptor Agonist FAUC 725; Bioorganic & Medicinal Chemistry Letters 12 (2002) 2377-2380.

Harald Huebner et al: Conjugated Enynes as Nonaromatic Catechol Bioisosteres: Synthesis, Binding Experiments, and Computational Studies of Novel Dopamine Receptor Agonists Recognizing Preferentially the D3 Subtype; J. Med. Chem. 2000, 43, 756-762.

Karin Schlotter et al: Fancy Bioisosteres: Metallocene-Derived G-Protein-Coupled Receptor Ligands with Subnanomolar Binding Affinity and Novel Selectivity Profiles; J. Med. Chem. 2005, 48, 3696-3699.

International Search Report mailed Jan. 20, 2011; PCT/EP2010/070194; Int'l File Date: Dec. 20, 2010; 4 pages.

Peter Gmeiner et al: Azaindole-Derivatives II: Synthesis and Analgesic Effect of Pyrazolo[1,5-a]pyridines; Arch. Pharm. (1988), 321, 517-520—translation of the paragraphs on p. 517, col. 1, line 13 to col. 2, line 7.

H.H. Coenen et al: Iodinated Radiopharmaceuticals, Radioiodination Reactions for Pharmaceuticals, Compendium for Effective Synthesis Strategies, 2006, Springer.

International Preliminary Report on Patentability issued Jun. 26, 2012; PCT/EP2010/070194; Int'l File Date: Dec. 20, 2010; 4 pages.

H.H. Coenen; Fluorine-18 Labeling Methods: Features and Possibilities of Basic Reactions; 36 pages, 2007.

A.S. Horn; Synthesis and radioreceptor binding activity of N-o437, a new, extremely potent and selective D2 dopamine receptor agonist; vol. 7 -1985 Pharmaceutisch Weekblad Scientific Edition; 4 pages.

* cited by examiner

Figure 1: Functional activity of the compounds 1 and 2 in comparison to the activity of the reference serotonin (5-HT) at the human 5-HT1a serotonin receptor
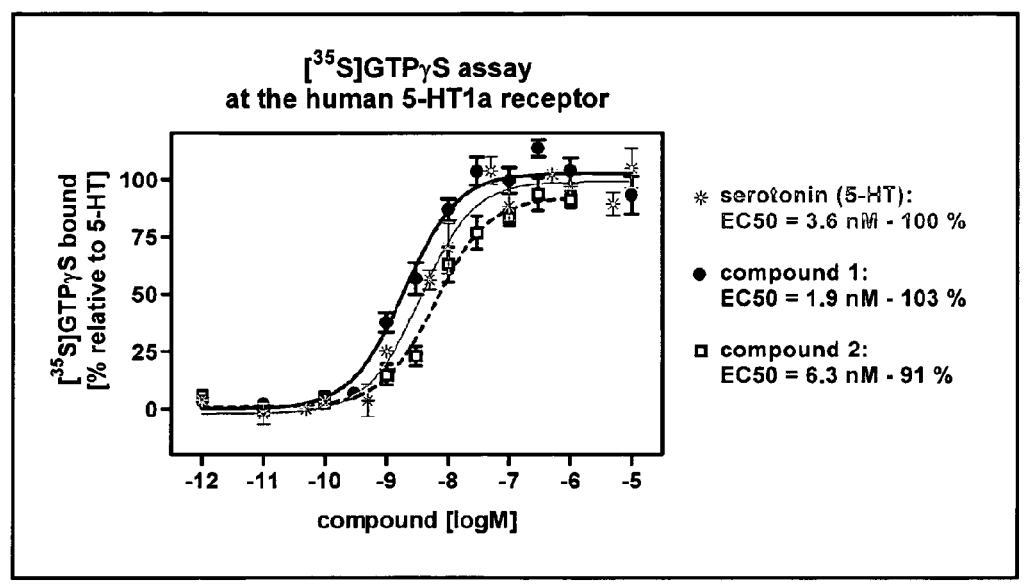

Figure 2: Inhibition of licking time in the mouse formalin assay after oral administration of compound 1
(a) Oral administration of 3 mg/kg compound 1
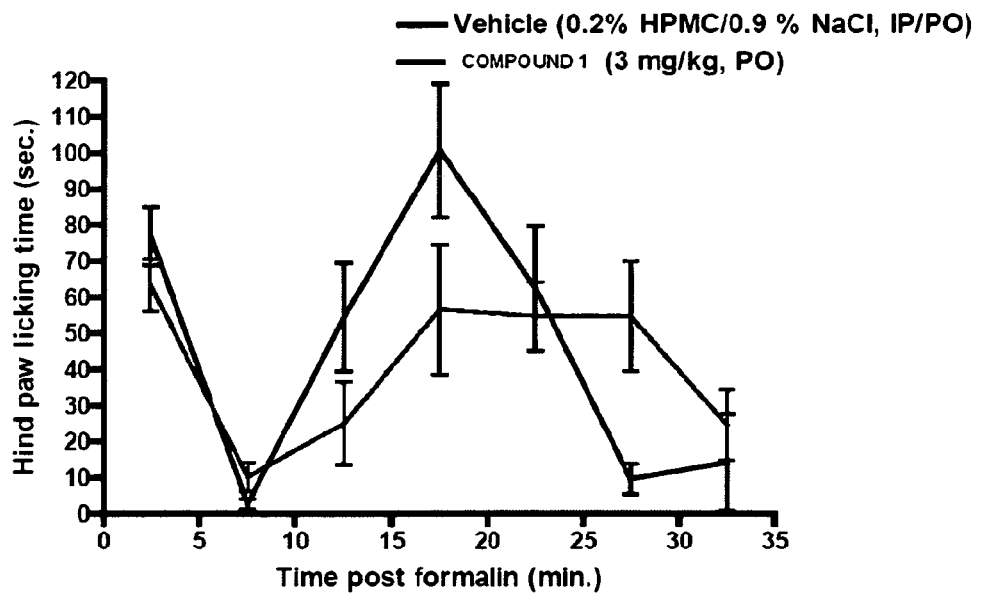
(b) Oral administration of 10 mg/kg compound 1
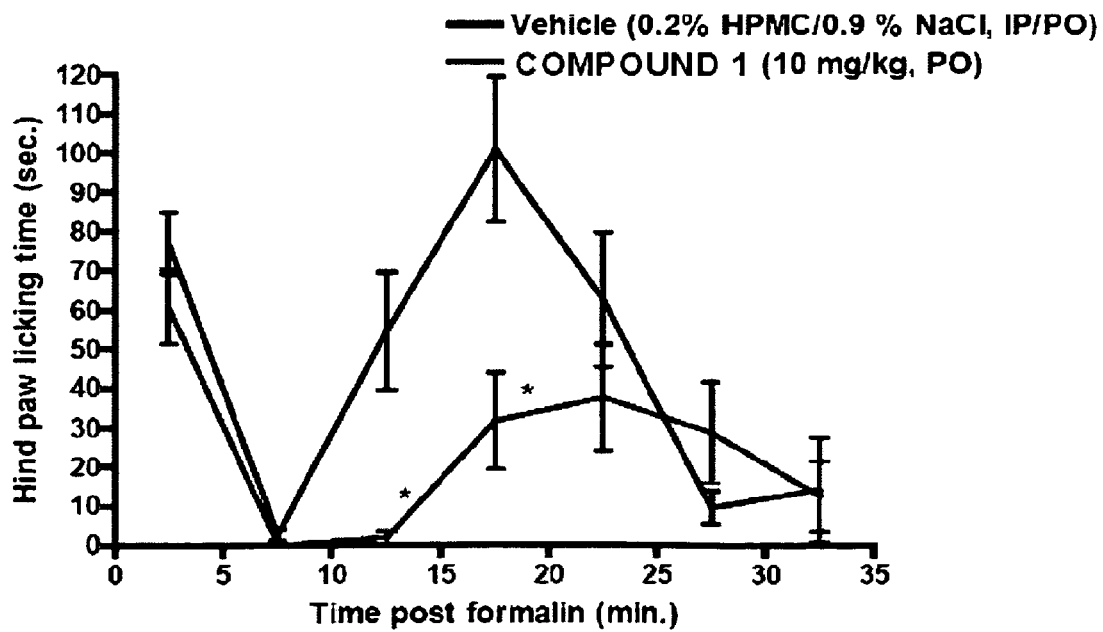

Figure 3: XRPD spectrum of the crystalline base of compound 1
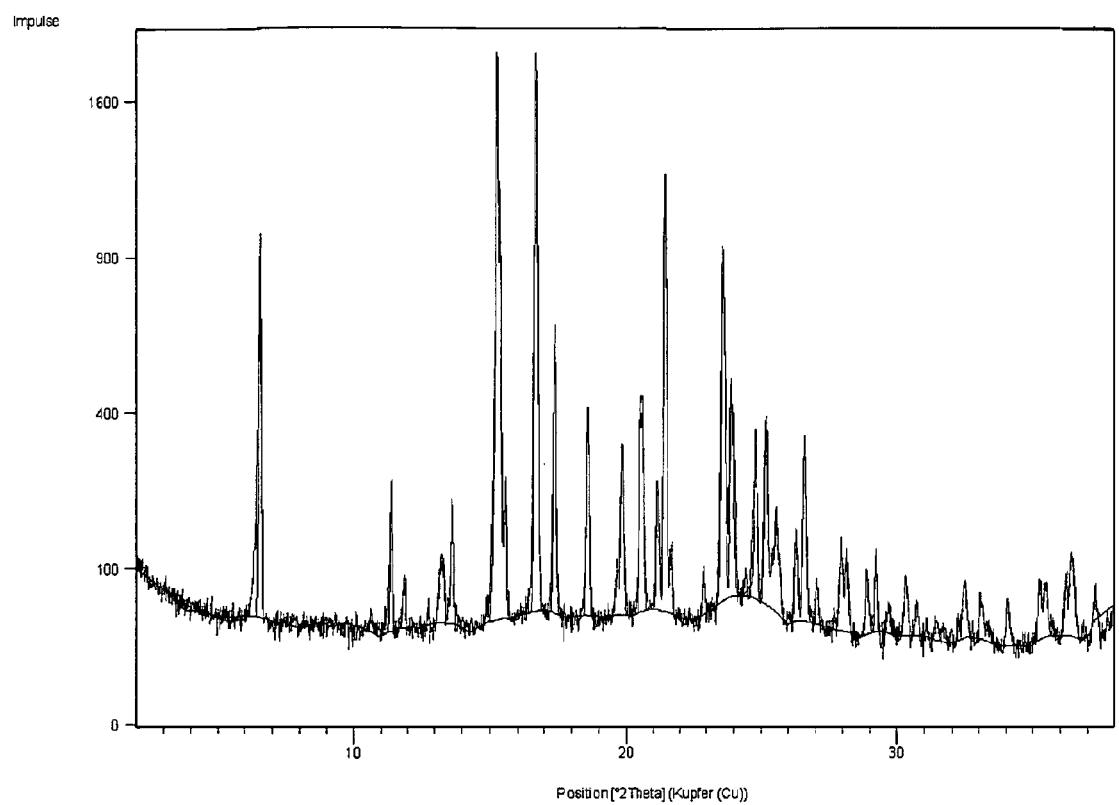

AMINOTETRALINE DERIVATIVES

I. BACKGROUND OF THE INVENTION

Dysfunction of the serotonin 5-HT1a receptor (5-HT1a) is thought to play a role in the pathogenesis of various disorders such as pain, anxiety and panic disorders, attention deficit and hyperactivity disorder (ADHD) or depression (see e.g. Savitz, Progress in Neurobiology 2009, 88, pages 17-31).

Accordingly, selective serotonin reuptake inhibitors (SSRIs) such as fluoxetine, sertraline, paroxetine or citalopram have had significant success in treating depression and related diseases. However, due to their indirect mode of action on the serotonin receptors, SSRIs stimulate serotonergic receptors non-selectively and via a significant delay taking several weeks for the drug to begin reaching its full potential. Also, SSRIs require sufficient endogenous serotonin and in general have been found to be effective in only up to about 50-60% of the patients.

For this reason, directly acting 5-HT1a agonists have been developed.

Buspirone was possibly the $1^{st}$ direct 5-HT1a agonist, which was approved as a human drug for the treatment of generalized anxiety disorder in the $80^{th}$. However, the bioavailability of buspirone is very low; moreover, buspirone is a partial 5-HT1a agonist with remarkable affinity to other receptors such as the dopamine D1 and with an undesirable affinity to adrenergic alpha receptors. There was thus the need for alternative 5-HT1a agonists.

Gepirone and tandospirone are both partial and selective 5-HT1a agonists which share a 4-pyrimidin-2-ylpiperazinyl-butyl partial structure with buspirone. While the approval of gepirone for treating anxiety and depression was refused by the American Food and Drug Administration in 2007, tandospirone is only available in China and Japan for treating anxiety and major depressive disorder.

8-Hydroxy DPAT is a compound which is known as full 5-HT1a agonists (Arvidsson et al, J Med Chem 1981, Vol 24.8, p 921; Arvidsson et al, J Med Chem 1984, Vol 27.1, p 45). However, the compound has only been used as a research tool, inter alia because of its very low oral bioavailability (Mason et al, Xenobiotica, 1995, Vol 25.12, p 1371). Also, while 8-OH-DPAT was originally described to have no significant dopaminergic activity it later turned out that the compound also has certain affinity to the D3 receptor (Lejeune, J Pharmacol Exp Ther 1997, Vol 280.3, p 1241).

Various derivatives of 8-OH-DPAT have been published in the $80^{th}$ and $90^{th}$ with the aim to improve the pharmacokinetic properties of aminotetralines. These derivatives are mainly based on a modification of the tetraline scaffold such as e.g. annelation to a third ring, leading to orally available benzindol-8-amino derivatives (Hansson, Eur J Med Chem 1997, Vol 32, p 571; Ennis, J Med Chem 1995, Vol 38, p 2217). However, unfortunately this family of benzindoles has been shown to have mutagenic potential by being tested positive in the Ames test (Stjernlöf, J Med Chem 1993, Vol 36, p 2059).

Although various other direct and selective 5-HT1a agonists have been described in literature, none of them have been widely approved for human use up to now. Examples are disclosed in WO 03/106449, WO2009/060030, WO 02/83666, WO 02/60423, WO 04/14915, WO 05/90300, WO 05/12291, or WO 99/65887.

A need therefore exists to provide alternative 5-HT1a agonists.

Preferably, such 5-HT1a agonists are full agonists showing at least about 70%, preferably at least about 80%, more preferably at least about 90%, more preferably at least about 95% activity, even more preferably about 100% agonist activity compared to serotonin in a functional 5-HT1a assay.

In one instance it may be desirable to have partial agonists at the 5-HT1a receptor thus exhibiting between about 30 and about 70% serotonergic activity.

In one instance it is also desirable that such new 5-HT1a ligands are selective 5-HT1a modulators showing significant selectivity to the phylogenetically related dopaminergic and adrenergic receptors. For example, in certain instances it would be advantageous if the new 5-HT1a agonists would have a selectivity to at least one, preferably of two, more preferably of all of D1, D2, D3 and D4 receptors of at least a factor 30, more preferably at least a factor 50, and even more preferably at least a factor of 100, 200 or more.

In contrast, and depending on the disease to be treated it may be advantageous in certain cases if such new 5-HT1a agonists also exhibit significant dopaminergic activity, preferably to the D2 and/or D3 receptor. For example, in the treatment of certain movement disorders related to the dopaminergic system, a 5-HT1a agonists may be desirable that also exhibits D2 and/or D3 affinity thus showing an affinity to the 5-HT1a receptor with a selectivity to D2 and/or D3 of less than about a factor 30, more preferably less then about a factor 20, or 10.

Desirably, the new 5-HT1a agonists are orally available or can be delivered through biological membranes such as the skin or mucosa. For example, it could be of advantage if the new 5-HT1a agonists can be administered transdermally, preferably by passive transdermal systems such as patches.

II. DESCRIPTION OF THE INVENTION

One embodiment relates to compounds of the general formula I

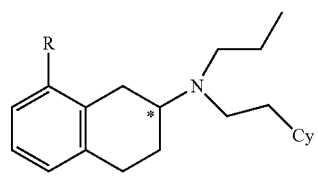

wherein
the * indicates an asymmetric centre,
R is OR1, di(C1-C3)alkylamino, S(C1-C3)alkyl, SH or NHR3;
R1 is hydrogen, a group —C(=O)R2, —SO$_2$CF$_3$, or (C1-C3)alkyl which is unsubstituted or substituted with one or more halogen atoms,
R2 is (C1-C6)alkyl, (C1-C6)alkyloxy, phenyl, phenyl(C1-C3)alkyl or phenyl(C1-C3)alkyloxy, wherein the phenyl group is optionally substituted which one or more substituents selected from (C1-C3)alkoxy, (C1-C3)alkyl, halogen, or CF$_3$,
R3 is hydrogen, (C1-C3)alkyl, formyl, (C1-C3)alkylcarbonyl, (C1-C3)alkoxycarbonyl, or (C1-C3)alkylaminocarbonyl;
Cy is an aromatic, heteroaromatic or non-aromatic cyclic group X, Y or Z, wherein
X is a 5 or 6 membered aromatic or heteroaromatic ring which is unsubstituted or substituted with one or two groups R4,
Y is a bicyclic aromatic or heteroaromatic ring system which is unsubstituted or substituted with one to three groups R5 and which ring system is selected from among

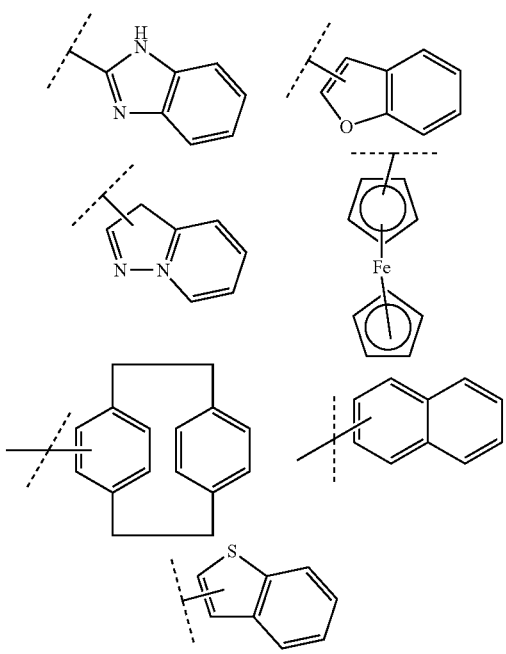

wherein the bond crossed by a dotted line indicates the attachment site of the group Y to the aminotetraline scaffold;
each R4 and R5 is independently selected from halogen, hydroxyl, (C1-C6)alkyl, preferably (C1-C3)alkyl, (C1-C6) alkoxy, preferably (C1-C3)alkoxy, or $CF_3$, wherein each alkyl or alkoxy may be substituted with one or more halogens or a hydroxyl group; and
Z is adamantyl which is unsubstituted or substituted with methyl and/or hydroxyl
including its enantiomers, solvates and pharmaceutically acceptable salts.

Surprisingly, it has been found that the compounds disclosed herein have strong affinity to the 5-HT1a receptor. A summary of the binding affinities to the 5-HT1a serotonin and to other related G-protein coupled receptors is shown in Table 1 further below.

It has also been found, surprisingly, that the selectivity to the other tested receptors, in particular to the dopaminergic receptors can be steered by the appropriate selection and combination of the groups R and Cy, as further described herein. This allows the design of desired features (e.g. highly selective 5-HT1a agonists or combined 5-HT1a/D2/D3 agonists) depending on the underlying disease.

In one embodiment, in the compounds of formula I R is OR1.

In one embodiment of the present invention, R is OR1 and R1 is methyl, hydrogen, —$SO_2CF_3$ or a group —C(=O)R2 wherein R2 is (C1-C6)alkyl, (C1-C6)alkoxy, phenyl, or phenyl(C1-C3)alkyl, wherein the phenyl group is optionally substituted which one or more substituents selected from methoxy, methyl, halogen. Preferably, R2 is (C1-C6)alkyl.

In one embodiment of the invention, in the compounds of formula I Cy is a 5 or 6 membered aromatic or heteroaromatic ring which may be selected from the group of phenyl, thienyl, furanyl, imidazolyl, 1,2,3-triazolyl, 1,2,4-triazolyl, pyrazolyl, pyridyl, pyrimidyl, and which ring maybe unsubstituted or substituted with one or two groups R4, as defined further above.

In another embodiment of the invention, Cy in formula I is adamantyl optionally substituted with methyl and/or hydroxyl, preferably unsubstituted adamantyl. In one embodiment, Cy is Z, preferably adamantly, and R is O(C1-C3)alkyl or S(C1-C3)alkyl, preferably, OMe or SMe.

In another embodiment, Cy in the compounds of formula I is a bicyclic aromatic or heteroaromatic ring system Y which is unsubstituted or substituted with one, two or three groups R5 and which ring system is selected from among

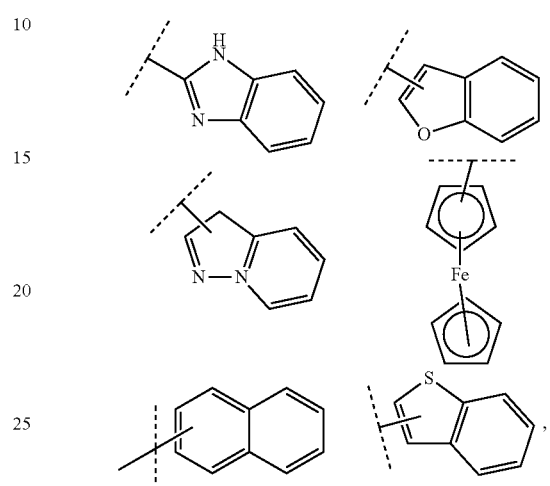

wherein each R5 is independently selected from halogen, hydroxyl, (C1-C3)alkyl, or (C1-3)alkoxy, wherein each alkyl or alkoxy may be substituted with a hydroxyl group or one or more halogens, such as to form e.g. the group $CF_3$. In one embodiment R5 is fluoro, bromo, chloro, methyl, ethyl, methoxy, ethoxy, hydroxymethyl, hydroxyethyl or the group $CF_3$.

In one embodiment of the invention, Cy in formula I is ferrocenyl.

In one embodiment, Cy is benzofuran or benzthiophen, each of which is optionally substituted with one to three groups R5. In one embodiment, Cy is benzimidazole optionally substituted with one, two or three groups R5. In one embodiment, Cy is a pyrazolo[1,5a]pyridine optionally substituted with one, two or three groups R5.

One embodiment relates to compounds of formula I, wherein
R is hydroxyl or (C1-C3)alkoxy, preferably methoxy, and
Cy is selected from the group of thienyl, preferably, thien-2-yl, phenyl, adamantyl, preferably adamant-1-yl, ferrocenyl, preferably ferrocen-1-yl, and [2.2]paracyclophanyl, preferably [2.2]paracyclophan-4-yl, wherein the thienyl or phenyl may independently be unsubstituted or substituted with one to two groups independently selected from among hydroxyl, (C1-C3)alkyl, preferably methyl and (C1-C3)alkoxy, preferably methoxy, including its enantiomers, crystals, solvates and pharmaceutically acceptable salts.

One preferred embodiment relates to compounds having the general formula II

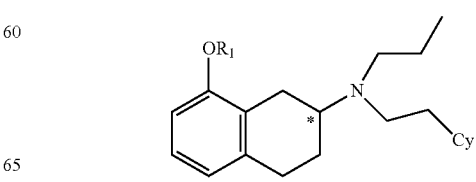

wherein
R1 is hydrogen, a group —C(=O)R2, or (C1-C3)alkyl which is unsubstituted or substituted with one or more halogen atoms;
R2 is (C1-C6)alkyl, (C1-C6)alkyloxy, phenyl, phenyl(C1-C3)alkyl or phenyl(C1-C3)alkyloxy, wherein the phenyl group is optionally substituted which one or more substituents selected from (C1-C3)alkoxy, (C1-C3)alkyl, halogen, or $CF_3$;
Cy is a 5 or 6 membered aromatic or heteroaromatic ring selected from the group of phenyl, thienyl, furanyl, imidazolyl, 1,2,3-triazolyl, 1,2,4-triazolyl, pyrazolyl, pyridyl, pyrimidyl, and which ring maybe unsubstituted or substituted with one or two groups R4;
each R4 is independently selected from halogen, (C1-C3) alkyl, or (C1-C3)alkoxy, wherein each alkyl or alkoxy may be substituted with one or more halogens or a hydroxyl group, including its enantiomers, solvates and pharmaceutically acceptable salts.

In one preferred embodiment R in formula I is OR1 and R1 in the compounds of formula I and II is hydrogen.

In another preferred embodiment, R in formula I is OR1 and R1 in the compounds of formula I and II represents a group C(=O)R2 wherein R2 is (C1-C6)alkyl, (C1-C6)alkyloxy, phenyl, phenyl(C1-C3)alkyl or phenyl(C1-C3)alkyloxy, wherein the phenyl group is optionally substituted which one or more substituents selected from (C1-C3)alkoxy, (C1-C3)alkyl, halogen, or $CF_3$. Such a group may be cleaved off in vivo by esterases thus releasing the hydroxyl function on the aminotetralin ring. Since the hydroxyl function is believed one hand to strongly contribute both to the high affinity to the 5-HT1a receptor, and to high selectivity over other G-protein coupled receptors but on the other hand to potentially negatively impact on bioavailability, such compounds with an ester function in the 8-position may represent valuable prodrugs. In a preferred embodiment, R2 is (C1-C6) alkyl, (C1-C6)alkyloxy, phenyl, or benzyl. In one preferred embodiment R2 is (C1-C3)alkyl.

Accordingly, in one embodiment of the present invention R in the compounds of formula I is OR1 and R1 in the compounds of formula I or II is selected from hydrogen or a group C(=O)R2, wherein R2 is as described above, and preferably represents (C1-C6)alkyl, (C1-C6)alkyloxy, phenyl, or benzyl, wherein the phenyl ring (also as part of the benzyl group) may be unsubstituted or substituted with one or more methoxy, methyl and/or halogen.

Compounds of formula I or II with a more lipophilic group in the 8-position such as e.g. (C1-C3)alkoxy generally have a slightly inferior affinity/selectivity compared to those with a hydroxyl group in the 8-position but may have certain advantages in bioavailability. In one embodiment, R is OR1 and R1, also in formula II, is methyl.

In one embodiment in formula I or II, R is OR1 and R1, also in formula II, is hydrogen or methyl.

In one preferred embodiment, in the compounds of the present disclosure, Cy is thienyl or phenyl which is unsubstituted or substituted with one or two groups R4, which are selected from halogen, hydroxyl, (C1-C3)alkyl, or (C1-C3) alkoxy, wherein each alkyl or alkoxy may be substituted with one or more halogen atoms or a hydroxyl group.

In one embodiment,
(a) Cy in the compounds of formula I or II is thienyl or phenyl which is unsubstituted or substituted with one or two groups R4, which are selected from halogen, hydroxyl, (C1-C3) alkyl, or (C1-C3)alkoxy, wherein each alkyl or alkoxy may be substituted with one or more halogen atoms (such as e.g. to form the group $CF_3$) or a hydroxyl group; and (b) R in formula I is OR1, and R1 in formula I and II may be hydrogen, methyl or a group C(=O)R2, wherein R2 is (C1-C6)alkyl, (C1-C6)alkyloxy, phenyl, or benzyl, and preferably represents (C1-C3)alkyl.

In one embodiment,
(a) Cy in the compounds of formula I or II is thienyl or phenyl which is unsubstituted or substituted with one or two groups R4, which are selected from fluoro, chloro, bromo, hydroxyl, methyl, ethyl, methoxy, ethoxy, hydroxymethyl, hydroxyethyl, hydroxymethoxy, hydroxyethoxy, $CF_3$ or $C_2H_2CF_3$ and
(b) R in formula I is OR1, and R1 in formula I and II may be hydrogen, methyl or a group C(=O)R2, wherein R2 is (C1-C6)alkyl, (C1-C5)alkyloxy, phenyl, or benzyl, and preferably represents (C1-C4)alkyl.

In one embodiment, Cy is phenyl which is unsubstituted or substituted with one or two groups R4 which are selected from halogen, preferably fluoro, chloro or bromo, hydroxyl, methyl, methoxy or ethoxy.

In one embodiment Cy is thien-2-yl which is unsubstituted or substituted with one group R4 which is selected from (C1-C3)alkyl, halogen or (C1-C3)alkoxy, preferably fluoro, chloro, bromo, hydroxyl, methyl, methoxy or ethoxy.

In one embodiment Cy is unsubstituted thienyl, preferably unsubstituted thien-2-yl.

One preferred embodiment of the present invention relates to compounds of formula II in which R1 is hydrogen or methyl and Cy is phenyl or thienyl, preferably thien-2-yl, wherein the phenyl is optionally substituted with one or two groups R4 which are independently selected from halogen, (C1-C3)alkyl, (C1-C3)alkoxy, or $CF_3$.

One preferred embodiment relates to compounds of formula II, wherein R1 is hydrogen or a group —C(=O)R2 wherein R2 is (C1-6)alkyl, phenyl, or benzyl, wherein the phenyl may be optionally substituted as described further above, and Cy is thien-2-yl, preferably unsubstituted thien-2-yl.

One embodiment relates to the compounds specifically disclosed in the experimental section of the present invention and particularly in Tables 1 and 2 herein.

Preferred compound according to the present invention are
Another preferred embodiment relates to a compound selected from the group of
N-(8-Hydroxytetralin-2-yl)-N-propyl-N-[2-(2-thienyl) ethyl]amine (Compound 1)
(R)—N-(8-Hydroxytetralin-2-yl)-N-propyl-N-[2-(2-thienyl)ethyl]amine (Compound 1a)
(S)—N-(8-Hydroxytetralin-2-yl)-N-propyl-N-[2-(2-thienyl) ethyl]amine (Compound 1b)
N-(8-Methoxytetralin-2-yl)-N-propyl-N-[2-(2-thienyl) ethyl]amine (Compound 2)
(R)—N-(8-Methoxytetralin-2-yl)-N-propyl-N-[2-(2-thienyl)ethyl]amine (Compound 2a)
(S)—N-(8-Methoxytetralin-2-yl)-N-propyl-N-[2-(2-thienyl) ethyl]amine (Compound 2b)
N-(8-Hydroxytetralin-2-yl)-N-(2-phenylethyl)-N-propylamine (Compound 3)
N-(8-Methoxytetralin-2-yl)-N-(2-phenylethyl)-N-propylamine (Compound 4)
N-[2-(4-Hydroxyphenyl)ethyl]-N-(8-hydroxytetralin-2-yl)-N-propylamine (Compound 5)
N-[2-(4-Methoxyphenyl)ethyl]-N-(8-methoxytetralin-2-yl)-N-propylamine (Compound 6)
N-[2-(2,5-Dimethylphenyl)ethyl]-N-(8-hydroxytetralin-2-yl)-N-propylamine (Compound 7)
N-[2-(2,5-Dimethylphenyl)ethyl]-N-(8-methoxytetralin-2-yl)-N-propylamine (Compound 8)

N-[2-(1-Adamantyl)ethyl]-N-(8-hydroxytetralin-2-yl)-N-propylamine (Compound 9)
N-[2-(1-Adamantyl)ethyl]-N-(8-methoxytetralin-2-yl)-N-propylamine (Compound 10)
N-(2-Ferrocenylethyl)-N-(8-hydroxytetralin-2-yl)-N-propylamine (Compound 11)
N-(2-Ferrocenylethyl)-N-(8-methoxytetralin-2-yl)-N-propylamine (Compound 12)
N-(8-Hydroxytetralin-2-yl)-N-[2-([2.2]paracyclophan-4-yl)ethyl]-N-propylamine (Compound 13), and
N-(8-Methoxytetralin-2-yl)-N-[2-([2.2]paracyclophan-4-yl)ethyl]-N-propylamine (Compound 14)

Another preferred embodiment relates to compounds selected from
N-(8-Hydroxytetralin-2-yl)-N-propyl-N-[2-(2-thienyl)ethyl]amine
(R)—N-(8-Hydroxytetralin-2-yl)-N-propyl-N-[2-(2-thienyl)ethyl]amine
(S)—N-(8-Hydroxytetralin-2-yl)-N-propyl-N-[2-(2-thienyl)ethyl]amine
N-(8-Methoxytetralin-2-yl)-N-propyl-N-[2-(2-thienyl)ethyl]amine
(R)—N-(8-Methoxytetralin-2-yl)-N-propyl-N-[2-(2-thienyl)ethyl]amine
N-(8-Hydroxytetralin-2-yl)-N-propyl-N-(2-phenylethyl)amine
N-(8-Methoxytetralin-2-yl)-N-propyl-N-(2-phenylethyl)amine Other examples of compounds according to the current invention are
Acetic acid 7-[N-propyl-N-[2-(2-thienyl)ethyl]amino]tetralin-1-yl ester
4-Hydroxybutanoic acid 7-[N-propyl-N-[2-(2-thienyl)ethyl]amino]tetralin-1-yl ester
5-Hydroxypentanoic acid 7-[N-propyl-N-[2-(2-thienyl)ethyl]amino]tetralin-1-yl ester
Carbonic acid ethyl 7-[N-propyl-N-[2-(2-thienyl)ethyl]amino]tetralin-1-yl ester
N-(8-Hydroxytetralin-2-yl)-N-propyl-N-[2-(3-thienyl)ethyl]amine
N-(8-Methoxytetralin-2-yl)-N-propyl-N-[4-(3-thienyl)ethyl]amine
N-(2-Benzo[b]thienylethyl)-N-(8-hydroxytetralin-2-yl)-N-propylamine
N-(2-Benzo[b]thienylethyl)-N-(8-methoxytetralin-2-yl)-N-propylamine
N-(3-Benzo[b]thienylethyl)-N-(8-hydroxytetralin-2-yl)-N-propylamine
N-(3-Benzo[b]thienylethyl)-N-(8-methoxytetralin-2-yl)-N-propylamine
N-(8-Hydroxytetralin-2-yl)-N-propyl-N-(2-pyrazolo[1,5-a]pyridinylethyl)amine
N-(8-Methoxytetralin-2-yl)-N-propyl-N-(2-pyrazolo[1,5-a]pyridinylethyl)amine
N-(8-Hydroxytetralin-2-yl)-N-propyl-N-(3-pyrazolo[1,5-a]pyridinylethyl)amine
N-(8-Methoxytetralin-2-yl)-N-propyl-N-(3-pyrazolo[1,5-a]pyridinylethyl)amine
N-(8-Methylthiotetralin-2-yl)-N-propyl-N-[2-(3-thienyl)ethyl]amine
N-(8-Aminotetralin-2-yl)-N-propyl-N-[2-(3-thienyl)ethyl]amine
N-(8-Methylaminotetralin-2-yl)-N-propyl-N-[2-(3-thienyl)ethyl]amine
N-(8-Dimethylaminotetralin-2-yl)-N-propyl-N-[2-(3-thienyl)ethyl]amine
7-[N-propyl-N-[2-(2-thienyl)ethyl]amino]tetralin-1-yl formamide
7-[N-propyl-N-[2-(2-thienyl)ethyl]amino]tetralin-1-yl carbamic acid ethyl ester It was found, surprisingly, that compound 1, N-(8-hydroxytetralin-2-yl)-N-propyl-N-[2-(2-thienyl)ethyl]amine, was active in an oral animal model of pain (FIG. 1) and is able to penetrate skin in an in vitro skin model of transdermal penetration (Table 4). Accordingly, N-(8-hydroxytetralin-2-yl)-N-propyl-N-[2-(2-thienyl)ethyl]amine and its derivatives and close analogs disclosed herein are believed to be suitable for oral and/or transdermal administration.

A particularly preferred embodiment relates to the compound N-(8-hydroxytetralin-2-yl)-N-propyl-N-[2-(2-thienyl)ethyl]amine, including its individual enantiomers, and pharmaceutically acceptable salts thereof.

The present disclosure generally relates to the free bases of the respective compounds as well as to pharmaceutically acceptable salts as defined herein. In some embodiments, the free base may be particularly suited such as e.g. in transdermal applications. In other embodiments, salts may have certain advantages.

One specific embodiment relates to the base of N-(8-hydroxytetralin-2-yl)-N-propyl-N-[2-(2-thienyl)ethyl]amine, which may be in amorphous or crystalline form. In a preferred embodiment, the base is in crystalline form. In one embodiment, the base is in crystalline form 1 having main XRPD peaks at about 15.27; 16.68; 21.45; 23.60 degrees±0.2 deg 2-theta measured using Cu k-alpha radiation (lambda=1.540 Å). In one embodiment, the base of N-(8-hydroxytetralin-2-yl)-N-propyl-N-[2-(2-thienyl)ethyl]amine is in crystalline form 1 having additional XRPD peaks at about 6.56; 15.18; 15.38; 17.37; 23.93; 25.17 degrees±0.2 deg 2-theta. In one embodiment the crystalline base of compound 1 shows most or substantially all of the XRPD 2-theta peaks displayed in Table 5 or FIG. 3 herein. In one embodiment, the melting point of form 1, as determined by DSC, is at about 97-99° C.

Another embodiment relates to pharmaceutically acceptable salts of the presently disclosed compounds. Non limiting examples of pharmaceutically acceptable salts are given in the definitions of this application.

One embodiment relates to salts of the presently disclosed compounds, which are formed with optically active, enantiomerically pure organic acids. Such enantiopure organic acids may crystallize with one particular enantiomeric form of the compounds disclosed herein or with synthetic precursors/intermediates thereof thus facilitating an enantiomeric separation of the compounds and/or its synthesis intermediates from racemates or other enantiomeric mixtures, as further disclosed in the synthetic part of this application. Examples of such organic acids are tartaric acid, dibenzoyltartaric acid and its derivatives, cinnamoyltartaric acid and its derivatives, mandelic acid, malic acid, camphoric acid, N-acetylphenylalanine, camphorsulfonic acid or cyclic phosphorous acid esters like 4-(2-chlorophenyl)-2-hydroxy-5,5-dimethyl-1,3,2-dioxaphosphorinane-2-oxide.

One particular embodiment are salts or cocrystals of (R)— or (S)—N-(8-hydroxytetralin-2-yl)-N-propyl-N-[2-(2-thienyl)ethyl]amine and its intermediates as disclosed in the synthetic part, with enantiopure organic acids, preferably with (L)- or (D)-tartaric acid, (R,R)- or (S,S)-dibenzoyltartaric acid or cyclic phosphorous acid esters like (R)- or (S)-4-(2-chlorophenyl)-2-hydroxy-5,5-dimethyl-1,3,2-dioxaphosphorinane-2-oxide, preferably with (R,R)- or (S,S)—O,O-dibenzoyltartaric acid and 4-(R)- or 4-(S)-4-(2-chlorophenyl)-2-hydroxy-5,5-dimethyl-1,3,2-dioxaphosphorinane-2-oxide, respectively. A preferred embodiment is the salt (R)—N-(8-hydroxytetralin-2-yl)-N-propyl-N-[2-(2-thienyl)ethyl]amine (L)-(−)-(R,R)—O,O-dibenzoyltartaric acid, particularly in crystalline form.

Among the individual enantiomers, those compounds in which the carbon atom marked with an * in formula I and II, is in the (R) configuration have been shown to have a somewhat improved receptor profile compared to the respective (S) enantiomer, and are thus preferred. Accordingly, one embodiment relates to compounds, wherein at least about 70%, more preferably more than about 80%, 90%, 95%, 96%, 97%, 98% or even more than about 99% of the compound is in the (R)-configuration, i.e. the corresponding (S) enantiomer is present in less than about 30%, 20%, 10%, 5%, 4%, 3%, 2%, or even less then about 1%.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature with the most abundant isotope(s) being preferred. Examples of isotopes that can be incorporated into compounds of the invention include isotopes of hydrogen, carbon, nitrogen, oxygen, sulphur, fluorine and chlorine such as $H^2, H^3, C^{11}, C^{13}, C^{14}, N^{15}, N^{17}, O^{18}, S^{35}, F^{18}$, and $Cl^{36}$, respectively. Certain isotopic variations of the invention, for example, those in which a radioactive isotope such as $H^3$ or $C^{14}$ is incorporated, are useful in drug and/or substrate tissue distribution studies. Tritiated, i.e., $H^3$, and carbon-14, i.e., $C^{14}$, isotopes are particularly preferred for their ease of preparation and detectability. Further, substitution with isotopes such as deuterium, i.e., $H^2$, may afford certain therapeutic advantages resulting form greater metabolic stability, for example, increased in vivo half-life, reduced dosage requirements and hence may be preferred in some circumstances. Isotopic variations of the compounds of the invention can generally be prepared by conventional procedures using appropriate isotopic variations of suitable reagents.

Also part of the invention are those compounds wherein at least one atom has been replaced by an isotope of a different atom that can be used in vivo imaging techniques such as SPECT or PET. Examples for such derivatives usable in SPECT studies are compounds wherein a $T^{99m}$, $In^{111}$, $Rb^{82}$, $Cs^{137}$, $I^{123}$, $Ga^{67}$, $Ir^{192}$ or $Tl^{201}$, and preferably $I^{123}$ has been introduced (for iodination see e.g.: "Radioiodination Reactions for Pharmaceuticals, Compendium for Effective Synthesis Strategies" by Coenen H H, Springer, Dordrecht 2006), while for PET applications $C^{11}$, $N^{13}$, $O^{15}$, $F^{18}$, $Rb^{82}$, $Sr^{82}$, and preferably $F^{18}$ ("Fluorine-18 labeling methods: Features and possibilities of basic reactions" by Coenen, H H, Ernst Schering Res Found Workshop 2007, Vol 62, p 15-50; Miller, P W Ang Chem Int Ed 2008, Vol 47, p 8998) may be used.

The compounds of the present disclosure can be used in therapy, particularly in human therapy.

For the administration as a medicinal drug, the compounds may be used in pharmaceutical composition comprising a compound of the present disclosure, and a pharmaceutically acceptable carrier, as further defined herein. Such a pharmaceutical composition can be adapted for example for oral, intravenous, intramuscular, subcutaneous, nasal, rectal, buccal or transdermal administration and may comprise pharmaceutically acceptable carriers, adjuvants, diluents, stabilizers and the like.

For instance, the compounds of the present invention may be dissolved in oils, propylene glycol or other solvents which are commonly used to produce an injection. Suitable examples of the carriers include, but not limited to, physiological saline, polyethylene glycol, ethanol, vegetable oils, isopropyl myristate, etc. The compounds of the present invention may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

In one embodiment, the compounds of the present invention may be administered orally, e.g. in the form of a tablet, a capsule, a drage', a powder, a granulate, or in form of a liquid or a semi-solid, by way of non-limiting example.

Oral formulations may contain, without limitation, sustained release agents, disintegrants, fillers, lubricants, stabilizers, antioxidants, flavours, dispersion agents, electrolytes, buffers, dyes, or conservation agents. Suitable excipients and formulations are known to those skilled in the art and are disclosed in standard monographs such as like Remington ("The science and practice of pharmacy", Lippincott, Williams & Wilkins, 2000). Typical sustained release agents are for example those that swell upon contact with water such as polyvinylpyrrolidone, hydroxyethylcellulose, hydroxypropylcellulose, other cellulose ethers, starch, pregelatinised starch, polymethacrylate, polyvinylacetate, microcrystalline cellulose, dextrans, and mixtures of these. Non-limiting examples of disintegrants include pregelatinised starch, sodium starch glycolate, microcrystalline cellulose, carboxymethylcellulose sodium (CMC-Na), cross-linked CMC-Na, and low-substituted hydroxypropylcellulose, as well as mixtures thereof. Suitable fillers and binders include without limitation microcrystalline cellulose, powdered cellulose, lactose (anhydrous or monohydrate), compressible sugar, starch (e.g. corn starch or potato starch), pregelatinised starch, fructose, sucrose, dextrose, dextrans, other sugars such as mannitol, maltitol, sorbitol, lactitol and saccharose, siliconised microcrystalline cellulose, calcium hydrogen phosphate, calcium hydrogen phosphate dihydrate, dicalciumphosphate dihydrate, tricalciumphophate, calcium lactate or mixtures thereof. Lubricants, antiadherents and/or glidants include stearic acid, magnesium stearate, calcium stearate, sodium lauryl sulphate, hydrogenated vegetable oil, hydrogenated castor oil, sodium stearyl fumarate, macrogols, glycerol dibehenate, talc, corn starch, silicon dioxide, and the like, including mixtures.

In a preferred embodiment, the compounds are administered transdermally. This mode of administration prevents the so-called $1^{st}$ pass effect of oral administration and moreover allows providing more constant plasma levels which is of particular advantage in some instances. The design of transdermal systems such as e.g. patches or electrophoretic devices is generally known from the art, see e.g. Venkatraman and Gale, Biomaterials 1998, Vol 19, p 1119; Prausnitz and Langer, Nat Biotechnology 2008, Vol 26.11 p 1261; WO 2001/47503; WO2009/000262; WO99/49852; WO 07/094876.

Accordingly, one embodiment relates to pharmaceutical compositions comprising the compounds disclosed herein, wherein the pharmaceutical composition is a transdermal system, and preferably is a patch, such as e.g. of the monolithic "drug-in-adhesive" or of the reservoir type.

In a particularly preferred embodiment of the present disclosure, the transdermal patch comprises N-(8-hydroxytetralin-2-yl)-N-propyl-N-[2-(2-thienyl)ethyl]amine, preferably enantiopure in the form of its (R)-enantiomer, either as the free base or as a pharmaceutically acceptable salt.

The preferable dose level of the compounds according to the present invention depends upon a variety of factors including the condition and body weight of the patient, severity of the particular disease, dosage form, and route and period of administration, but may appropriately be chosen by those skilled in the art. In various embodiments, the compounds are administered in an amount ranging from 0.001 to 10 mg/kg of body weight per day, or from 0.03 to 1 mg/kg of body weight per day. Individual doses may range from about 0.1 to 100 mg of active ingredient per day, from about 0.2 to 50 mg/day, or from about 0.3 to 20 mg/day. Doses may be administered once a day, or several times a day with each divided portions.

Another aspect of the present invention is a Kit comprising a medicine or a pharmaceutical composition as described above, and instructions for its use.

The medicine according to the present invention may comprise one of the presently disclosed compounds as "stand alone" treatment of a CNS disease. Alternatively, a presently disclosed compound may be administered together with other useful drugs in a combination therapy. In a non-limiting example, a compound according to the present invention is combined with another antidepressant medicament having a different mode of action. Likewise a compound of the present invention can be combined with an analgesic drug if a painful condition is to be treated. Also, a compound of the present disclosure may be used in combination with levodopa to treat Parkinson's disease and levodopa-associated dyskinesia. In combination therapies the two or more active principles may be provided via the same formulation or as a "kit of parts", i.e. in separate galenic units. Also, the two or more active principles may be administered to the patient at the same time or subsequently, e.g. in an interval therapy.

The compounds of the present invention are useful medicines, and may be used for the treatment and/or prevention of various diseases of the CNS system. One embodiment of the present disclosure is thus a compound as described herein for use as a medicine, in particular for use as a medicine for the treatment and/or prevention of a disease which is associated with a malfunction of the serotonin signaling system, examples of which are further disclosed below.

Because of their affinity to the serotonin 5-HT1a receptors, the present compounds in one embodiment can be used for the production of a medicament for the treatment or prevention of a variety of diseases such as Pain, particularly chronic pain (nociceptive and neuropathic), including for example
  neuropathic pain (central and peripheral) including mononeuropathies such as trigeminal neuralgia, and polyneuropathies, which may be associated with diseases such as diabetic neuropathy, herpetic or other infections, AIDS, or cancer
  postoperative pain
  inflammatory pain
treatment and prophylaxis of migraine
depression, such as for example
  endogenic depressions including major depression and depressive phases of bipolar disorders
  somatogenic depressions
  psychogenic depressions
anxiety disorders, such as generalized anxiety, panic disorders, certain kinds of phobia such as e.g. social phobia, and post-traumatic disorders
compulsive disorders and/or aggressive disorders
a psychotic disease including manic phases of bipolar disorder, acute idiopathic psychotic illnesses, psychoses associated with other diseases, drug-induced psychoses, and particularly schizophrenia;
attention deficit hyperactivity disorder (ADHD);
movement disorders, including
  idiopathic movement disorders such as e.g. idiopathic Parkinson's disease and it's associated motor disturbances such as tremors, akinesia, and dyskinesia; Segawa syndrome; or Tourette's syndrome
  drug-induced movement disorders, such as e.g. tardive dyskinesia or, particularly, levodopa-induced dyskinesia;
addiction disorders such as e.g. cocaine, alcohol, opiate and nicotine addiction;
sexual dysfunction, in particular male or female sexual response disorders, such as, particularly, male impotence;
amnesic and/or cognitive disorders,
autism, or disorders associated with autism;
stroke;
urinary incontinence; and/or
sleep disorders.

A further therapeutic application that can be mentioned is the treatment and/or prevention of neurodegenerative diseases, since due to the neuroprotective effect of 5-HT1a agonists, the substances may delay or stop the destruction or loss of neurones as the cause or result of a pathophysiological episode. Such illnesses are for example amyotrophic lateral sclerosis, Alzheimer's disease, Huntington's chorea, epilepsy, Parkinson's disease or other synucleopathies, such as e.g. of the Parkinson-plus-syndrome type.

Another embodiment of the present disclosure is a method of treating a subject having a disease as described above by administering a compound as described herein in a therapeutically effective amount. According to one aspect, the subject to be treated with the presently disclosed compounds is determined to be in need of a treatment of one or more of the above diseases based on a prior diagnosis of the disease or various diseases.

Definitions

"Adamantyl" refers to the radical of adamantane (tricyclo [$3.3.1.1^{3,7}$]decan)

"Alkyl" includes monovalent saturated aliphatic hydrocarbyl groups. The hydrocarbon chain may be either straight-chained or branched. Examples of "alkyl" include those with 1-6 carbon atoms ("(C1-C6)alkyl"), those with 1-5 carbon atoms ("(C1-C5)alkyl"), 1-4 carbon atoms ("(C1-C4)alkyl"), or only 1-3 carbon atoms ("(C1-C3)alkyl"). This term is exemplified by groups such as methyl, ethyl, n-propyl, iso-propyl, n-butyl, iso-butyl, tert-butyl, t-amyl, and the like.

"Alkylaminocarbonyl" refers to the group —C(=O)—NH-alkyl, wherein alkyl is defined above.

"Alkylcarbonyl" includes the group —C(=O)-alkyl, wherein alkyl is defined above.

"Alkyloxycarbonyl" refer to the radical —C(=O)—O—R, wherein R is an alkyl group as defined herein. In various embodiments, "alkyloxycarbonyl" is a (C1-C6)alkyloxycarbonyl group, (C1-C5)alkyloxycarbonyl group or a (C1-C3) alkyloxycarbonyl group.

"Alkyloxy" or "alkoxy" includes the group —OR wherein R is "alkyl" as defined and exemplified further above. Particular alkyloxy groups include, by way of example, methoxy, ethoxy, n-propoxy, isopropoxy, n-butoxy, tert-butoxy, sec-butoxy, n-pentoxy, 1,2-dimethylbutoxy, and the like.

"Dialkylamino" refers to the group —N-dialkyl, where "dialkyl" indicates two independent alkyl groups (defined above) bonded to the N atom. A non-limiting example of "dialkylaminocarbonyl" is —N-di(C1-C3)alkyl, wherein two individual alkyl groups each of up to three C-atoms are bound to the nitrogen atom.

"Formyl" refers to the group —CH=O

"Furanyl" refers to the aromatic heterocyclic radical of furane ($C_4H_4O$; oxacyclopentadiene)

"Halo" or "halogen" refers in particular to fluoro, chloro, bromo and iodo. Preferred halogen groups are either fluoro or chloro.

"Heteroaromatic" refers to an aromatic heterocycle, as defined herein. Whether a heteroaromatic group is substituted with one or more substituents, is specified throughout this specification and in the items.

"Heterocycle" refers to a compound comprising at least one cycle in which a ring forming atom is different from carbon.

"Hydroxyl" refers to the radical —OH.

"Imidazolyl" refers to the aromatic heterocyclic radical of imidazole ($C_3H_4N_2$; 1,3-diaza-2,4-cyclopentadiene).

"Phenyl" is the aromatic radical —$C_6H_5$.

"Phenoxy" or "Phenyloxy" comprises the group —O-phenyl, wherein "phenyl" has the meaning as defined further above.

"Phenylalkyl" is an "alkyl" group substituted with a phenyl group, wherein "alkyl" is as defined further above. For example, phenyl(C1-C6)alkyl refers to a (C1-C6)alkyl which is substituted with a phenyl group. Examples of phenylalkyl groups are phenylethyl and benzyl, wherein benzyl is a particularly preferred phenylalkyl group.

"Phenylalkyloxy" is an "alkyloxy" group substituted with a phenyl. Examples of phenylalkyloxy groups are phenylethyloxy and benzyloxy.

"Pyrazolyl" refers to the radical of pyrazole ($C_3H_4N_2$; 1,2-diazole).

"Pyridyl" refers to the radical of pyridine ($C_5H_5N$; azabenzene)

"Pyrimidinyl" refers to the radical of pyrimidine ($C_4H_4N_2$; 1,3 diazine)

"Thienyl" is the aromatic heterocyclic radical —$C_4H_3S$ of thiophene ($C_4H_4S$; thiacyclopentadiene).

"Triazolyl" refers to aromatic heterocyclic radical with the molecular formula $C_2H_2N_3$, having a five-membered ring of two carbon atoms and three nitrogen atoms.

"1,2,3-Triazolyl" and "1,2,4-triazolyl" refer to triazolyl residues, with the numbers specifying the positions of the N-atoms in the respective ring.

Unless expressly specified otherwise, any "alkyl", "phenyl", "heteroaryl", "furanyl", pyrazolyl" etc is meant to be unsubstituted. If any "alkyl", "phenyl", or "heteroaryl", is expressly stated to be substituted in a given substituent, this usually also refers to the respective "alkyl", "phenyl", or "heteroaryl" partial structures of more complex structures in the same substituent, such as "alkyloxy", "alkylsulfonyl", "phenoxy", "heteroaryloxy", etc.

In the present disclosure, a compound is thought to be "enantiomerically pure" or "enantiopure" if at least about 95%, preferably at least about 96%, 97%, 98%, even more preferably at least about 99% of the compound consists of a particular enantiomer, such as e.g. the (R)-enantiomer while the other enantiomer, such as e.g. the (S) enantiomer is present in less than about 5%, 4%, 3%, 2%, or even less than about 1%.

"Pharmaceutically acceptable" means generally considered as safe for use in pharmaceutical preparations, and preferably officially approved by a regulatory agency of the Federal or a state government for such use, such as e.g. by the US Food and Drug Administration (FDA), or the European medicine Agency (EMEA), and/or being listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. Other salts include 2,2-dichloroacetate, adipate, alginate, ascorbate, aspartate, 2-acetamidobenzoate, caproate, caprate, camphorate, cyclamate, laurylsulfate, edisilate, esylate, isethionate, formate, galactarate, gentisate, gluceptate, glucuronate, oxoglutarate, hippurate, lactobionate, napadisilate, xinafoate, nicotinate, oleate, orotate, oxalate, palmitate, embonate, pidolate, p-aminosalicylate, sebacate, tannate, rhodanide, undecylenate, and the like; or (2) salts formed when an acidic proton present in the parent compound is replaced, such as with ammonia, arginine, benethamine, benzathine, calcium, choline, deanol, diethanolamine, diethylammonium, ethanolamine, ethylendiamine, meglumine, hydrabamine, imidazole, lysine, magnesium, hydroxyethylmorpholine, piperazine, potassium, epolamine, sodium, trolamine, tromethamine or zinc.

"Pharmaceutically acceptable carrier" refers to a diluent, adjuvant, excipient, or carrier, or other ingredient with which a compound of the invention is administered and which is pharmaceutically acceptable as further defined herein.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the condition, age, weight, gender etc. of the subject to be treated.

"Treating" or "treatment" of any disease or disorder refers, in one embodiment, to ameliorating the disease or disorder (i.e., arresting or reducing the development of the disease or at least reducing one of the clinical symptoms of the disease). In another embodiment "treating" or "treatment" refers to ameliorating at least one physical parameter, which may or may not be discernible by the subject. In yet another embodiment, "treating" or "treatment" refers to modulating the disease or disorder, either physically (e. g. stabilization of a discernible on non discernible symptom), physiologically (e. g. stabilization of a physiological parameter), or both. In yet another embodiment, "treating" or "treatment" refers to delaying or preventing the onset or progression of the disease or disorder.

Specific Items of the Invention Specific embodiments of the inventions are the items 1-28 listed below. These items are non-limiting examples to further illustrate the invention, but shall not limit the disclosure and the scope of the present invention.

Items

1) A compound of formula I

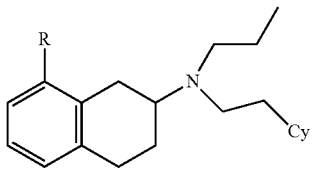

wherein

R is OR1, di(C1-C3)alkylamino, SH, S(C1-C3)alkyl or NHR3;

R1 is hydrogen, a group —C(=O)R2, —SO₂CF₃, or (C1-C3)alkyl which is unsubstituted or substituted with one or more halogen atoms, R2 is (C1-C6)alkyl, (C1-C6)alkyloxy, phenyl, phenyl(C1-C3)alkyl or phenyl(C1-C3)alkyloxy, wherein the phenyl group is optionally substituted with one or more substituents selected from (C1-C3)alkoxy, (C1-C3)alkyl, halogen, or CF₃;

R3 is hydrogen, (C1-C3)alkyl, formyl, (C1-C3)alkylcarbonyl, (C1-C3)alkoxycarbonyl, or (C1-C3)alkylaminocarbonyl;

Cy is an aromatic, heteroaromatic or non-aromatic cyclic group X, Y or Z, wherein X is a 5 or 6 membered aromatic or heteroaromatic ring which is unsubstituted or substituted with one or two groups R4;

Y is a bicyclic aromatic or heteroaromatic ring system which is unsubstituted or substituted with one to three groups R5 and which ring system is selected from among

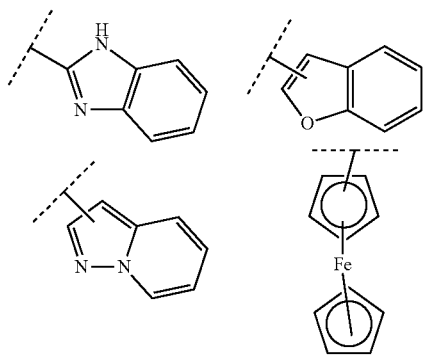

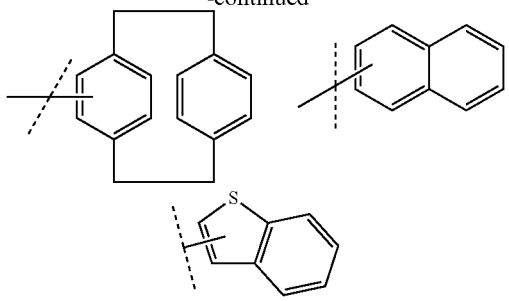

wherein the bond crossed by a dotted line indicates the attachment site of the group Y to the aminotetraline scaffold;

wherein each R4 and R5 is independently selected from halogen, hydroxyl, CF₃, C1-C3 alkyl, or C1-C3 alkoxy, wherein each alkyl or alkoxy may be substituted with one or more halogens or a hydroxyl group, and Z is adamantyl which is unsubstituted or substituted with methyl and/or hydroxyl including its enantiomers, crystals, solvates and pharmaceutically acceptable salts.

2) A compound according to item 1, wherein R is OR1.

3) A compound according to item 2, wherein R1 is methyl, hydrogen or a group —C(=O)R2 wherein R2 is (C1-C6) alkyl or (C1-C6)alkyloxy, preferably (C1-C6)alkyl.

4) A compound according to anyone of the preceding items wherein Cy is a 5 or 6 membered aromatic or heteroaromatic ring which is selected from the group of phenyl, thienyl, furanyl, imidazolyl, 1,2,3-triazolyl, 1,2,4-triazolyl, pyrazolyl, pyridyl, pyrimidyl, and unsubstituted or substituted with one or two groups R4.

5) A compound according to items 1-4, wherein Cy is unsubstituted adamantyl, preferably adamant-1-yl.

6) A compound according to items 1-4, wherein Cy is a bicyclic aromatic or heteroaromatic ring system Y which is unsubstituted or substituted with one to three groups R5 and which ring system is selected from among

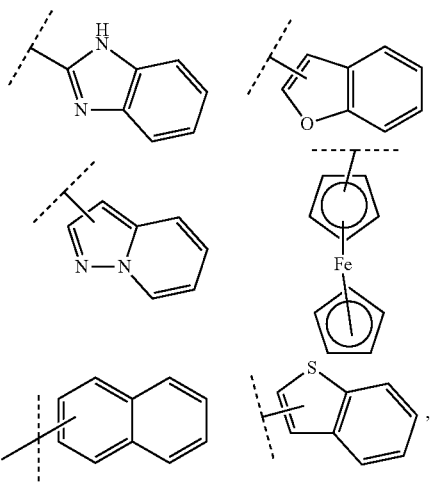

wherein each R5 is independently selected from halogen, hydroxyl, CF₃, (C1-C3)alkyl, or (C1-C3)alkoxy, wherein each alkyl or alkoxy may be substituted with one or more halogens or a hydroxyl group.

7) A compound having the general formula II

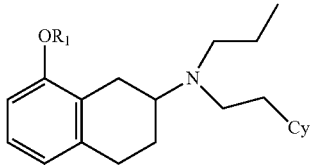

wherein
R1 is hydrogen, a group —C(=O)R2, or (C1-C3)alkyl which is unsubstituted or substituted with one or more halogen atoms,
R2 is (C1-C6)alkyl, (C1-C6)alkyloxy, phenyl, phenyl(C1-C3)alkyl or phenyl(C1-C3)alkyloxy, wherein the phenyl group is optionally substituted with one or more substituents selected from (C1-C3)alkoxy, (C1-C3)alkyl, halogen or $CF_3$,
Cy is a 5 or 6 membered aromatic or heteroaromatic ring selected from the group of phenyl, thienyl, furanyl, imidazolyl, 1,2,3-triazolyl, 1,2,4-triazolyl, pyrazolyl, pyridyl, pyrimidyl, each of which is unsubstituted or substituted with one or two groups R4,
each R4 is independently selected from halogen, (C1-C3) alkyl, or (C1-C3)alkoxy, wherein each alkyl or alkoxy may be substituted with one or more halogens or a hydroxyl group,
including its enantiomers, crystals, solvates and pharmaceutically acceptable salts.
8) A compound according to item 7, wherein R1 is hydrogen or a group —C(=O)R2 wherein R2 is (C1-C6)alkyl or (C1-C6)alkyloxy, preferably (C1-C3)alkyl.
9) A compound according to item 7, wherein R1 is methyl.
10) A compound according to items 1-3 or 7, wherein Cy is thienyl or phenyl which is unsubstituted or substituted with one or two groups R4, which are selected from halogen, hydroxyl, (C1-C3)alkyl, or (C1-C3)alkoxy, wherein each alkyl or alkoxy may be substituted with one or more halogen atoms or a hydroxyl group.
11) A compound according to items 1-3 or 7, wherein Cy is phenyl which is unsubstituted or substituted with one or two groups R4 which are selected from halogen, methyl, hydroxy, methoxy or ethoxy.
12) A compound according to items 1-3 or 7, wherein Cy is thien-2-yl which is unsubstituted or substituted with one group R4 which is selected from (C1-C3)alkyl, halogen, (C1-C3)alkoxy.
13) A compound according to items 1-3 or 7, wherein Cy is unsubstituted thienyl, preferably unsubstituted thien-2-yl.
14) A compound according to items 1-3 or 7, wherein R1 is hydrogen or methyl and Cy is phenyl or thienyl, preferably thien-2-yl, wherein the phenyl is optionally substituted with one or two groups R4 which are independently selected from halogen, hydroxyl, (C1-C3)alkyl, (C1-C3) alkoxy, or CF3.
15) A compound according to item 7, wherein R1 is hydrogen or a group —C(=O)R2 wherein R2 is (C1-C6)alkyl, and Cy is thien-2-yl, preferably unsubstituted thien-2-yl.
16) A compound according to item 1, wherein
R is hydroxyl or (C1-C3)alkoxy, preferably methoxy, and Cy is selected from the group of thienyl, preferably, thien-2-yl, phenyl, adamantyl, preferably adamant-1-yl, ferrocenyl, preferably ferrocen-1-yl, and [2.2]paracyclophanyl, preferably [2.2]paracyclophan-4-yl, wherein the thienyl or phenyl may independently be unsubstituted or substituted with one to two groups independently selected from among hydroxyl, (C1-C3)alkyl, preferably methyl and (C1-C3)alkoxy, preferably methoxy,
including its enantiomers, crystals, solvates and pharmaceutically acceptable salts.
17) A compound according to item 16, and selected from
N-(8-Hydroxytetralin-2-yl)-N-propyl-N-[2-(2-thienyl) ethyl]amine,
(R)—N-(8-Hydroxytetralin-2-yl)-N-propyl-N-[2-(2-thienyl)ethyl]amine,
(S)—N-(8-Hydroxytetralin-2-yl)-N-propyl-N-[2-(2-thienyl) ethyl]amine,
N-(8-Methoxytetralin-2-yl)-N-propyl-N-[2-(2-thienyl) ethyl]amine,
(R)—N-(8-Methoxytetralin-2-yl)-N-propyl-N-[2-(2-thienyl)ethyl]amine,
(S)—N-(8-Methoxytetralin-2-yl)-N-propyl-N-[2-(2-thienyl) ethyl]amine,
N-(8-Hydroxytetralin-2-yl)-N-(2-phenylethyl)-N-propylamine,
N-(8-Methoxytetralin-2-yl)-N-(2-phenylethyl)-N-propylamine,
N-[2-(4-Hydroxyphenyl)ethyl]-N-(8-hydroxytetralin-2-yl)-N-propylamine,
N-[2-(4-Methoxyphenyl)ethyl]-N-(8-methoxytetralin-2-yl)-N-propylamine,
N-[2-(2,5-Dimethylphenyl)ethyl]-N-(8-hydroxytetralin-2-yl)-N-propylamine,
N-[2-(2,5-Dimethylphenyl)ethyl]-N-(8-methoxytetralin-2-yl)-N-propylamine,
N-[2-(1-Adamantyl)ethyl]-N-(8-hydroxytetralin-2-yl)-N-propylamine,
N-[2-(1-Adamantyl)ethyl]-N-(8-methoxytetralin-2-yl)-N-propylamine,
N-(2-Ferrocenylethyl)-N-(8-hydroxytetralin-2-yl)-N-propylamine, and
N-(2-Ferrocenylethyl)-N-(8-methoxytetralin-2-yl)-N-propylamine,
including its enantiomers, crystals, solvates and pharmaceutically acceptable salts.
18) A compound according to item 1 and selected from
Acetic acid 7-[N-propyl-N-[2-(2-thienyl)ethyl]amino]tetralin-1-yl ester,
4-Hydroxybutanoic acid 7-[N-propyl-N-[2-(2-thienyl)ethyl] amino]tetralin-1-yl ester,
5-Hydroxypentanoic acid 7-[N-propyl-N-[2-(2-thienyl) ethyl]amino]tetralin-1-yl ester,
Carbonic acid ethyl 7-[N-propyl-N-[2-(2-thienyl)ethyl] amino]tetralin-1-yl ester,
N-(8-Hydroxytetralin-2-yl)-N-propyl-N-[2-(3-thienyl) ethyl]amine,
N-(8-Methoxytetralin-2-yl)-N-propyl-N-[2-(3-thienyl) ethyl]amine,
N-(2-Benzo[b]thienylethyl)-N-(8-hydroxytetralin-2-yl)-N-propylamine,
N-(2-Benzo[b]thienylethyl)-N-(8-methoxytetralin-2-yl)-N-propylamine,
N-(3-Benzo[b]thienylethyl)-N-(8-hydroxytetralin-2-yl)-N-propylamine,
N-(3-Benzo[b]thienylethyl)-N-(8-methoxytetralin-2-yl)-N-propylamine,
N-(8-Hydroxytetralin-2-yl)-N-propyl-N-(2-pyrazolo[1,5-a] pyridinylethyl)amine,
N-(8-Methoxytetralin-2-yl)-N-propyl-N-(2-pyrazolo[1,5-a] pyridinylethyl)amine, N-(8-Hydroxytetralin-2-yl)-N-propyl-N-(3-pyrazolo[1,5-a]pyridinylethyl)amine,
N-(8-Methoxytetralin-2-yl)-N-propyl-N-(3-pyrazolo[1,5-a]pyridinylethyl)amine,
N-(8-Methylthiotetralin-2-yl)-N-propyl-N-[2-(3-thienyl)ethyl]amine,
N-(8-Aminotetralin-2-yl)-N-propyl-N-[2-(3-thienyl)ethyl]amine,
N-(8-Methylaminotetralin-2-yl)-N-propyl-N-[2-(3-thienyl)ethyl]amine,
N-(8-Dimethylaminotetralin-2-yl)-N-propyl-N-[2-(3-thienyl)ethyl]amine,
7-[N-propyl-N-[2-(2-thienyl)ethyl]amino]tetralin-1-yl formamide, and
7-[N-propyl-N-[2-(2-thienyl)ethyl]amino]tetralin-1-yl carbamic acid ethyl ester
including its enantiomers, crystals, solvates and pharmaceutically acceptable salts.
19) N-(8-Hydroxytetralin-2-yl)-N-propyl-N-[2-(2-thienyl)ethyl]amine including its enantiomers, crystals solvates and pharmaceutically acceptable salts.
20) A salt of N-(8-Hydroxytetralin-2-yl)-N-propyl-N-[2-(2-thienyl)ethyl]amine and an enantiomerically pure organic acid, preferably tartaric acid or dibenzoyltartaric acid.
21) The base N-(8-Hydroxytetralin-2-yl)-N-propyl-N-[2-(2-thienyl)ethyl]amine
22) A compound according to anyone of the preceding items, and particularly the compounds of items 19, 20, and 21, wherein at least 90% of the compound is in the (R)-configuration.
23) A compound according to anyone of the preceding items for use in therapy.
24) A pharmaceutical composition comprising at least one compound according to anyone of the preceding items and a pharmaceutically acceptable carrier.
25) A pharmaceutical composition according to item 24 adapted for oral or transdermal administration.
26) The pharmaceutical composition of item 25, which is a transdermal patch.
27) The transdermal patch of item 26 comprising N-(8-Hydroxytetralin-2-yl)-N-propyl-N-[2-(2-thienyl)ethyl]amine or a pharmaceutically acceptable salt thereof.
28) Use of a compound according to anyone of items 1-22 for preparing a medicament for the treatment of a disease of the central nervous system, preferably of a disease which is associated with the disturbance of the serotonergic transmission.
29) Use according to item 28, wherein the disease is depression, an anxiety or panic disorder, attention deficit hyperactivity disorder (ADHD), sleep disorder, pain, a sexual disorder, or a movement disorder.
30) Use according to item 29, wherein the movement disorder is L-dopa associated dyskinesia.

III. EXPERIMENTAL PART

A. Synthesis

1. General Synthesis Schemes

A compound of formula I can be synthesized starting from 2-tetralones which are substituted in position 8 according to formula A1. Reductive amination of compounds of A1 utilizing propylamine and a hydride transferring reagent like sodium triacetoxyborohydride gives the secondary amines of formula A2 in good yields.

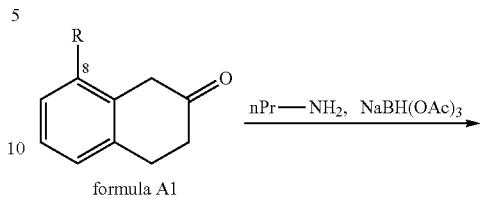

formula A1

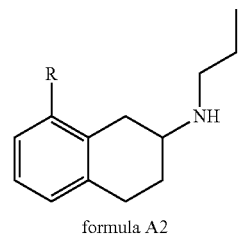

formula A2

Subsequent acylation of compounds of formula A2 results in amids according to formula A4. For this coupling reaction the acid derivatives according to formula A3 are used in an activated form as acid chlorides, acid bromides or acid anhydrids or, alternatively, as free acid compounds in the presence of an appropriate activating reagent typically used for amid coupling

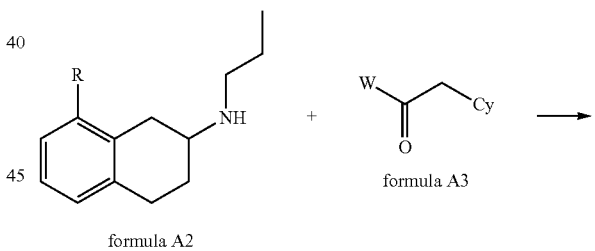

formula A2    formula A3

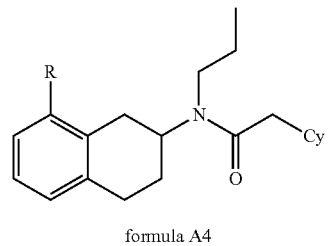

formula A4 wherein W is selected of hydroxyl, chloro, bromo or alkylcarbonyloxy;

and if W is hydroxyl, the corresponding acid derivative is activated by addition of an acid specific activating reagent like hydroxybenzotriazole, hydroxyazabenzotriazole, HATU (O-(7-azabenzotriazol-1-yl)-1,1,3,3-tetramethyluronium hexafluorophosphate) or TBTU (O-benzotriazolyl tetramethylisouronium tetrafluoroborate).

Reduction of the amid group of the compounds according to formula A4 in the presence of a reductive agent like lithium aluminiumhydride results in derivatives of formula A5 which represent the final compounds as embodiments of this disclosure

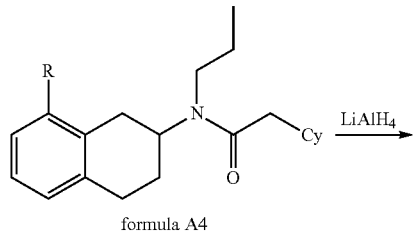

formula A4

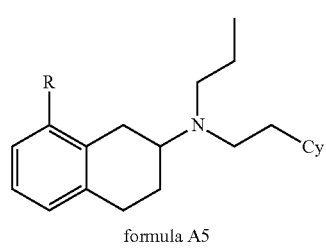

formula A5 and wherein in anyone of the formulas I, A1, A2, A3, A4 and A5

R and Cy are as defined further above and in the disclosures for compounds of formula I.

If R represents OR1 and if the final compounds shall be substituted by an 8-OH group (e.g. formula I; R=OH) a cleavage reaction with a compound according to formula A6 must be done. For example the acidic hydrolysis of an alkyloxy group in compound A6 (when R1=(C1-C3)alkyl) using strong mineralic acids like HBr, HCl, HI or $H_2SO_4$ or borohalide type Lewis acids like $BCl_3$ or $BBr_3$ reveals in the formation of compounds according to formula A7 representing further final compounds as embodiments of this disclosure

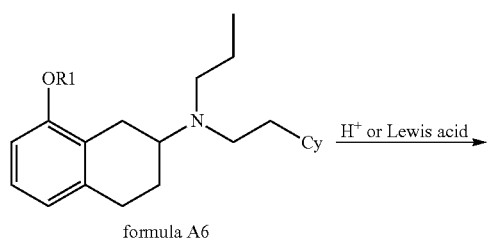

formula A6

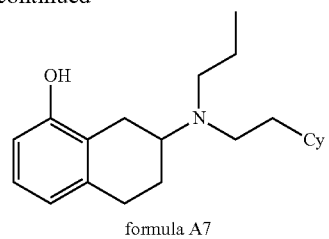

formula A7 wherein R1 and Cy are as defined further above and in the disclosures for compounds of formula I.

The synthesis of the enantiomerically pure embodiments starts from the racemic secondary amines according to formula A2 which are reacted with enantiochemically pure acids like (L)- or (D)-tartaric acid, (R,R)- or (S,S)-dibenzoyltartaric acid and its derivatives, (R,R)- or (S,S)-cinnamoyltartaric acid and its derivatives, (L)- or (D)-mandelic acid, (L)- or (D)-malic acid, (L)- or (D)-camphoric acid, (L)- or (D)-N-acetylphenylalanine, (L)- or (D)-camphorsulfonic acid or cyclic phosphorous acid esters like 4-(R)- or 4-(S)-4-(2-chlorophenyl)-2-hydroxy-5,5-dimethyl-1,3,2-dioxaphosphorinane-2-oxide to form diastereomeric salts. Stereochemical resolution of the resulting diastereomeric salts and subsequent liberation of the free base under basic conditions yields in the enantiopure secondary amines R-(A2) and S-(A2) according to formula A2a.

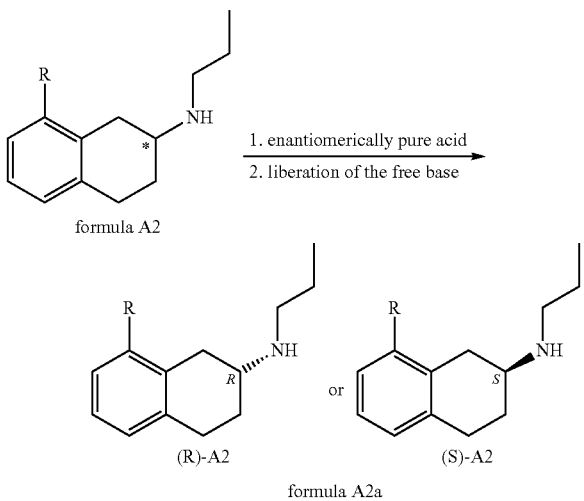

Subsequent reaction of the enantiomerically pure compounds R-(A2) or S-(A2) as described in detail above results in the formation of enantiopure compounds according to formula I representing final compounds as embodiments of this disclosure

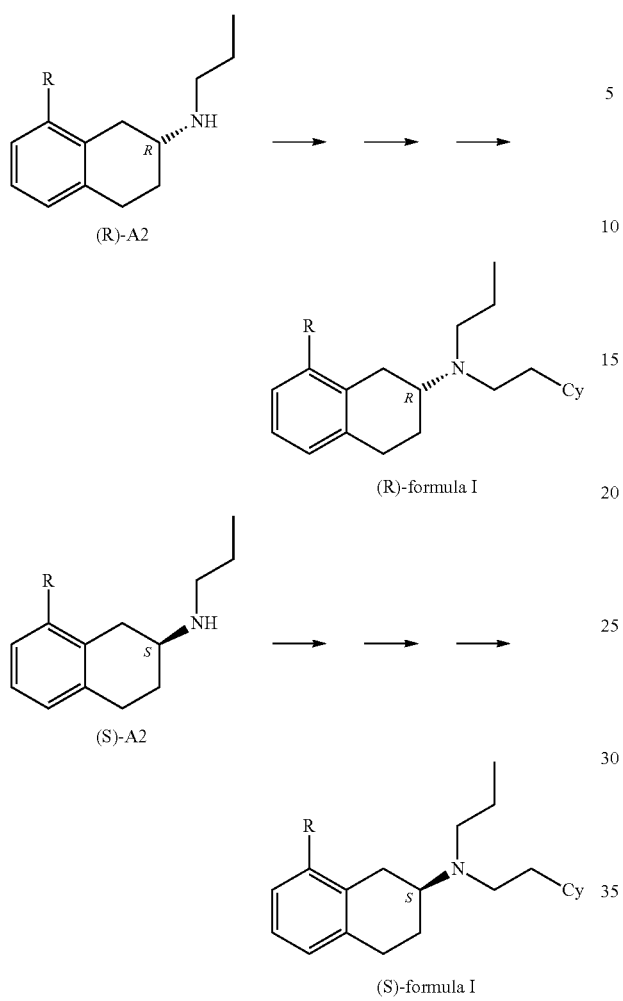

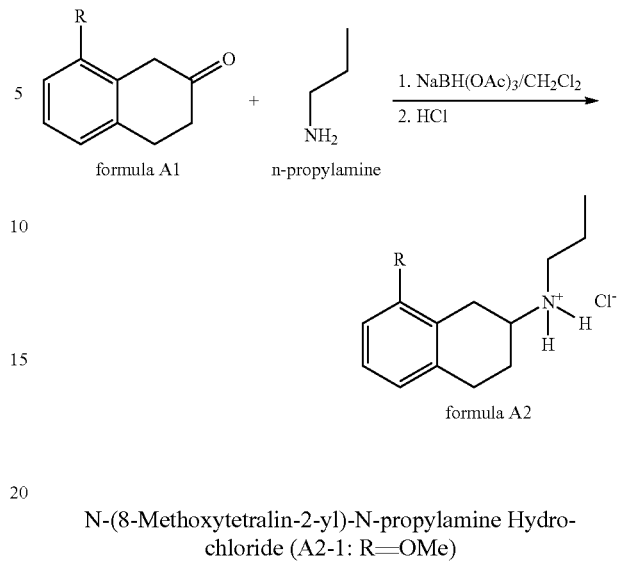

and wherein in anyone of the formulas I and A2a R and Cy are as defined further above and in the disclosures for compounds of formula I.

2 Synthesis of the Individual Compounds

2a. Synthesis of Secondary Amines According to Formula A2

The secondary amines of formula A2 were synthesized by reductive amination reaction of 8-substituted 2-tetralone derivatives according to formula A1 with n-propylamine. Reduction was accomplished in the presence of sodium triacetoxyborohydride in dry methylenchloride as solvent. The reaction was terminated by adding hydrochloric acid and the resulting amino hydrochloride was extracted from the aqueous phase under basic conditions and finally precipitated as hydrochloride to receive the secondary amines of type A2 in good yields with more than 75% yield.

N-(8-Methoxytetralin-2-yl)-N-propylamine Hydrochloride (A2-1: R=OMe)

To a solution of 5.1 g 8-methoxy-2-tetralone (A1-1: R=OMe) (purchased from Sigma-Aldrich, Munich (Germany); order number: 535451) (30 mmol) and 17 g NaBH(OAc)$_3$ (81 mmol) in 80 mL dry CH$_2$Cl$_2$ 4.9 mL n-Propylamin (59 mmol) were added dropwise. After stirring for 25 hrs at room temperature the solvent was evaporated, the residue resolved in conc. HCl and washed for several times with diethyl ether. The aqueous phase was basified with 5N NaOH and extracted with diethyl ether for several times, the collected organic layers were dried over Na$_2$SO$_4$ and the solvent was concentrated. Addition of 20 mL 2 M HCl (40 mmol) in diethyl ether and cooling at 4° C. resulted in precipitation of the hydrochloric salt, which was filtered and dried in vacuo to get a white solid.

Yield: 5.8 g (76%).

MP: 181° C. (literature: 191-193° C., for reference see: Naiman et al. J Med Chem 1989, Vol 32, p 253).

MS (EIMS): m/z 219 (M)$^+$. IR (NaCl) v (cm$^{-1}$): 3394, 2927, 1585, 1466, 1254, 1026 (free base). $^1$H NMR (CD$_3$OD, 600 MHz) δ (ppm): 1.07 (t, J=7.5 Hz, 3H), 1.74-1.84 (m, 3H), 2.31 (m, 1H), 2.59 (dd, J=16.6 Hz, 10.4 Hz, 1H), 2.87-2.97 (m, 2H), 3.10 (m, 2H), 3.29-3.34 (m, 1H), 3.48 (m, 1H), 3.82 (s, 3H), 6.72 (d, J=7.7 Hz, 1H), 6.77 (d, J=8.1 Hz, 1H), 7.13 (dd, J=8.1 Hz, 7.7H). $^{13}$C NMR (CD$_3$OD, 90 MHz) δ (ppm): 11.3, 21.0, 26.8, 27.4, 28.6, 47.8, 55.8, 56.0, 108.6, 121.8, 128.4, 137.2, 158.6.

HR-MS: C$_{18}$H$_{21}$ClFN$_3$OS; calculated: 381.1078. found: 381.1075.

The enantiomerically pure secondary amines of type (R)-A2 and (S)-A2 could be synthesized by reaction with 4-(R)- or 4-(S)-4-(2-chlorophenyl)-2-hydroxy-5,5-dimethyl-1,3,2-dioxaphosphorinane-2-oxide in ethanol resulting in formation of a diastereomeric salt, which was separated and crystallized in isopropanol. Liberation of the enantiopure secondary amines according to formula (R)-A2 and (S)-A2 was achieved by treatment with an aqueous solution of potassium hydroxide and extraction with methylenchloride. Alternatively, (R)-A2 could also be prepared by utilizing the enantiomerically pure (R,R)—O,O-dibenzoyl tartaric acid in ethanol.

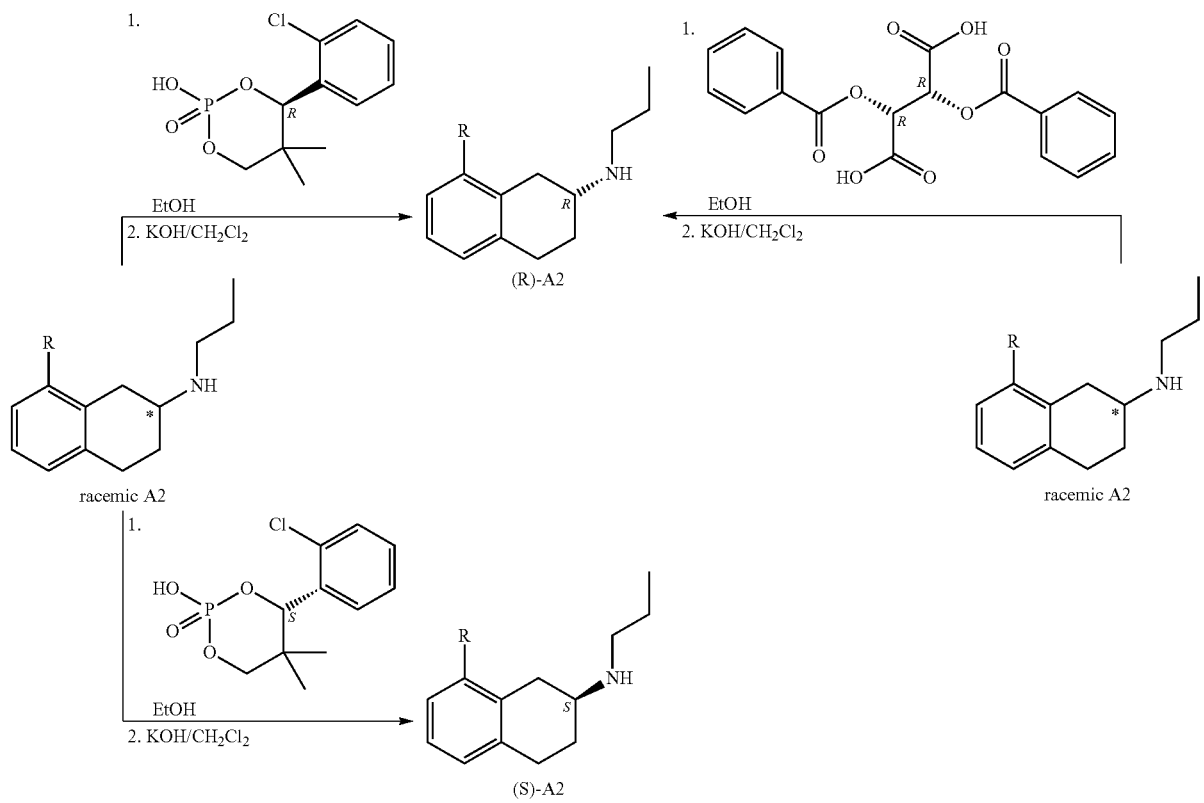

(R)—N-(8-Methoxytetralin-2-yl)-N-propylamine ((R)-A2-1: R=OMe)

To a solution of 720 mg (2.6 mmol) 4-(R)-4-(2-chlorophenyl)-2-hydroxy-5,5-dimethyl-1,3,2-dioxaphosphorinane-2-oxide in 30 mL EtOH a solution of 570 mg (2.6 mmol) racemic N-(8-methoxytetralin-2-yl)-N-propylamine (A2-1: R=OMe) (as the free base) in 15 mL EtOH was added and stirred for 40 min at room temperature. After evaporation of the solvent in vacuo the residue was resuspended in 25 mL of acetone and heated until reflux for 40 min. The solution was cooled down and stored at 4° C. for 20 hrs. The precipitate was recrystallized twice from isopropanol and dried to get the salt consisting of (R)—N-(8-methoxytetralin-2-yl)-N-propylamine and 4-(R)-4-(2-chlorophenyl)-2-hydroxy-5,5-dimethyl-1,3,2-dioxaphosphorinane-2-oxide.

Yield: 150 mg of a white solid (12%).

$[\alpha]_D^{25}$=+63.6° (in MeOH).

To liberate the free base (R)—N-(8-methoxytetralin-2-yl)-N-propylamine 140 mg of diastereomeric salt were dissolved in an aqueous solution of KOH and extracted for several times with methylenchloride. The organic layers were dried over $Na_2SO_4$, the solvent was evaporated in vacuo and the resulting residue was dried in vacuo to yield pure (R)—N-(8-methoxytetralin-2-yl)-N-propylamine ((R)-A2-1: R=OMe).

Yield: 58 mg of a yellow oil (91%).

MS, IR, $^1$H NMR and $^{13}$C NMR are identical with the data of compound A2-1.

$[\alpha]_D^{23}$=+80.1° (in MeOH).

Alternatively, to a solution of 160 mg (0.72 mmol) racemic N-(8-methoxytetralin-2-yl)-N-propylamine (A2-1: R=OMe) (as the free base) in 1.0 mL EtOH were added a solution of 270 mg (0.72 mmol) of (L)-(−)-O,O—(R,R)-dibenzoyltartaric acid monohydrate in 2.0 mL EtOH and stirred for 10 min at room temperature to get a fine white precipitate, which was filtered, washed with cold ethanol and suspended in 10% (v/v) aqueous KOH. After the extraction of the aqueous layer with methylenchloride for four times the organic layers were dried over $Na_2SO_4$, the solvent was evaporated in vacuo to get (R)—N-(8-methoxytetralin-2-yl)-N-propylamine ((R)-A2-1: R=OMe).

Yield: 130 mg of a yellow oil (82%).

MS, IR, $^1$H NMR and $^{13}$C NMR are identical with the data of compound A2-1.

$[\alpha]_D^{23}$=+67.0° (in MeOH).

(S)—N-(8-Methoxytetralin-2-yl)-N-propylamine ((S)-A2-1: R=OMe)

Synthesis worked similar according to the preparation of (R)-A2-1 when using 4-(S)-4-(2-chlorophenyl)-2-hydroxy-5,5-dimethyl-1,3,2-dioxaphosphorinane-2-oxide to get the diasteromeric salt consisting of (S)—N-(8-methoxytetralin-2-yl)-N-propylamine and 4-(S)-4-(2-chlorophenyl)-2-hydroxy-5,5-dimethyl-1,3,2-dioxaphosphorinane-2-oxide.

$[\alpha]_D^{23}$=−54.2° (in MeOH).

Liberation of the pure (S)—N-(8-methoxytetralin-2-yl)-N-propylamine ((S)-A2-1: R=OMe) could be achieved according to the protocol which is described for the liberation of (R)—N-(8-methoxytetralin-2-yl)-N-propylamine ((R)-A2-1: R=OMe).

Yield: 340 mg of a colorless oil (17%).

MS, IR, $^1$H NMR and $^{13}$C NMR are identical with the data of compound A2-1.

$[\alpha]_D^{23}$=−70.9° (in MeOH).

2b. Synthesis of Amides According to Formula A4

The formation of the amides according to formula A4 was achieved by coupling the secondary amine A2 with the acid chloride of an appropriate acid derivative of formula A3 (W=Cl) in dry chloroform in the presence of triethylamine as a base. If the secondary amine was provided as a hydrochloric salt, the free base had to be liberated before coupling.

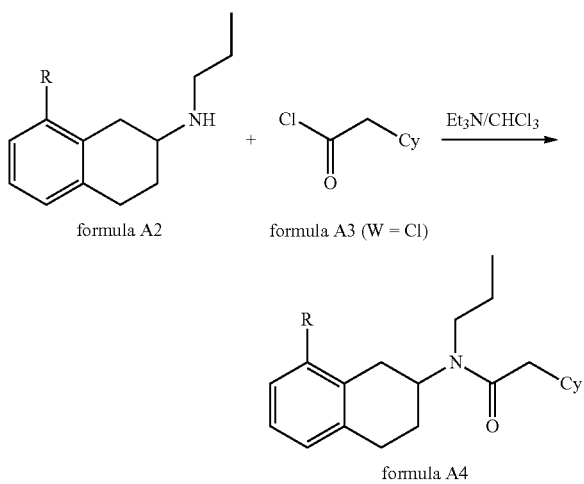

Alternatively, if necessary, the coupling reaction could be achieved by using the free acid derivative according to formula A3 (W=OH), which was dissolved in DMF in the presence of diisopropylethylamine (DIPEA) and which was furthermore activated by the reagent O-(7-azabenzotriazol-1-yl)-1,1,3,3-tetramethyluronium hexafluorophosphate (HATU).

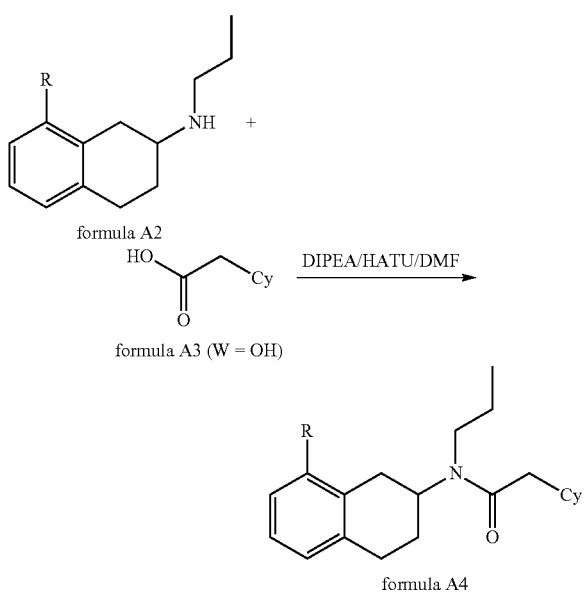

Most of the applied acid derivatives according formula A3 can be purchased from established suppliers of fine chemicals for synthesis. If not stated otherwise all acid derivatives of this invention were purchased from Acros Organics, Geel (Belgium), Alfa Aesar, Karlsruhe (Germany), Maybridge, Tintagel, Cornwall (UK) or Sigma-Aldrich, Munich (Germany).

N-(8-Methoxytetralin-2-yl)-N-propyl-2-(2-thienyl)acetamide (A4-1: R=OMe, Cy=2-thienyl)

A solution of 60 mg (0.27 mmol) of the free base of N-(8-methoxytetralin-2-yl)-N-propylamine (A2-1) and 0.11 mL $Et_3N$ (0.79 mmol) in 5 mL dry $CHCl_3$ was cooled in an ice bath. After adding 0.05 ml (0.41 mmol) 2-thienylacetic acid chloride (A3-1: W=Cl, Cy=2-thienyl) to the mixture the ice bath was removed and the reaction was stirred for 2 hrs at room temperature. In a second step further 0.05 mL (0.41 mmol) of 2-thienylacetic acid chloride (A3-1) were added and the reaction stirred for 20 hrs. The mixture was washed with a saturated solution of aqueous $NaHCO_3$ for several times and finally extracted with $CH_2Cl_2$. The organic layers were dried over $MgSO_4$ and the solvent was evaporated in vacuo. Flash chromatography of the residue on silica gel with a mixture of hexane/ethyl acetate 40/1 gave the product N-(8-methoxytetralin-2-yl)-N-propyl-2-(2-thienyl)acetamide.

Yield: 69 mg of a yellow oil (74%).

MS (EIMS): m/z 343 $(M)^+$. IR (NaCl) $\nu$ $(cm^{-1})$: 3386, 2924, 2881, 1639, 1458, 1254, 1068. $^1H$ NMR ($CDCl_3$, 360 MHz) $\delta$ (ppm): 0.90 (t, J=7.5 Hz, 3H), 1.55-1.87 (m, 3H), 1.87-1.96 (m, 1H), 2.62 (m, 1H), 2.74-3.03 (m, 3H), 3.23 (m, 2H), 3.79 (s, 3H), 3.83-4.02 (m, 2H), 4.08 (m, 1H), 6.61-6.73 (m, 2H), 6.85-6.98 (m, 2H), 7.08 (dd, J=7.9 Hz, 5.1 Hz, 1H), 7.18 (dd, J=5.1 Hz, 1.0 Hz, 1H). $^{13}C$ NMR ($CDCl_3$, 150 MHz) $\delta$ (ppm): 11.4, 11.6, 22.6, 24.8, 26.7, 27.3, 28.1, 28.2, 29.8, 29.8, 35.6, 35.9, 44.1, 46.6, 51.8, 54.8, 55.2, 106.9, 107.0, 120.8, 120.8, 123.5, 124.2, 124.6, 124.7, 125.8, 125.8, 126.3, 126.6, 126.7, 136.4, 136.9, 137.2, 137.2, 157.3, 157.4, 169.5, 169.9.

(R)—N-(8-Methoxytetralin-2-yl)-N-propyl-2-(2-thienyl)acetamide ((R)-A4-1: R=OMe, Cy=2-thienyl)

Synthesis worked according to the preparation of A4-1 when using 39 mg (0.18 mmol) enantiomerical pure (R)—N-(8-methoxytetralin-2-yl)-N-propylamine ((R)-A2-1: R=OMe) and 0.05 mL (0.41 mmol) 2-thienyl acetic acid chloride. Flash chromatography was done with hexane/ethyl acetate 20/1.

Yield: 50 mg of a yellow oil (81%).

MS, IR, $^1H$ NMR and $^{13}C$ NMR are identical with the data of compound A4-1.

$[\alpha]_D^{27}=+70.6°$ (in MeOH).

(S)—N-(8-Methoxytetralin-2-yl)-N-propyl-2-(2-thienyl)acetamide ((S)-A4-1: R=OMe, Cy=2-thienyl)

Synthesis worked according to the preparation of A4-1 when using 310 mg (1.4 mmol) enantiomerical pure (S)—N-(8-methoxytetralin-2-yl)-N-propylamine ((R)-A2-1: R=OMe) and 0.35 mL (2.8 mmol) 2-thienyl acetic acid chloride. Flash chromatography was done with hexane/ethyl acetate 20/1.

Yield: 340 mg of a yellow oil (70%).

MS, IR, $^1H$ NMR and $^{13}C$ NMR are identical with the data of compound A4-1.

$[\alpha]_D^{22}=-25.6°$ (in MeOH).

N-(8-Methoxytetralin-2-yl)-N-propyl-2-phenylacetamide (A4-2: R=OMe, Cy=phenyl)

Synthesis worked according to the preparation of A4-1 when using 120 mg (0.55 mmol) N-(8-methoxytetralin-2-yl)-N-propylamine (A2-1: R=OMe) and 0.11 mL (0.83 mmol) phenylacetic acid chloride (A3-2: W=Cl, Cy=phenyl). Flash chromatography was done with hexane/ethyl acetate 10/1.

Yield: 140 mg of colorless oil (78%).
MS (EIMS): m/z 337 (M)$^+$. IR (NaCl) v (cm$^{-1}$): 3356, 2962, 2931, 1639, 1585, 1466, 1254, 1115. $^1$H NMR (CDCl$_3$, 360 MHz) δ (ppm): 0.85-0.94 (m, 3H), 1.54-1.82 (m, 3H), 1.92 (m, 1H), 2.54-2.70 (m, 1H), 2.73-3.02 (m, 3H), 3.19 (m, 2H), 3.74 (s, 2H), 3.79 (s, 3H), 3.96-4.69 (m, 1H), 6.67 (m, 2H), 7.09 (dd, J=7.8 Hz, 7.7 Hz, 1H), 7.19-7.37 (m, 5H). $^{13}$C NMR (CDCl$_3$, 90 MHz) δ (ppm): 11.5, 11.7, 22.7, 24.8, 26.9, 27.5, 28.0, 28.1, 29.9, 31.9, 41.4, 42.0, 44.0, 46.6, 51.7, 54.6, 55.2, 106.9, 107.0, 120.8, 120.8, 123.7, 124.4, 126.2, 126.6, 126.6, 126.7, 128.5, 128.6, 128.8, 135.7, 136.5, 137.0, 157.4, 157.4, 170.6, 171.0.
CHN (%): C$_{22}$H$_{27}$NO$_2$ calculated (×0.1 H$_2$O): C, 77.89; H, 8.08; N, 4.13. found: C, 77.75; H, 7.82; N, 4.26.

N-(8-Methoxytetralin-2-yl)-N-propyl-2-(4-methoxyphenyl)acetamide (A4-3: R=OMe, Cy=4-methoxyphenyl)

Synthesis worked according to the preparation of A4-1 when using 110 mg (0.52 mmol) N-(8-methoxytetralin-2-yl)-N-propylamine (A2-1: R=OMe) and 0.12 mL (0.79 mmol) 4-methoxyphenylacetic acid chloride (A3-3: W=Cl, Cy=4-methoxyphenyl). Flash chromatography was done with hexane/ethyl acetate 10/1.

Yield: 160 mg of colorless oil (88%).
MS (EIMS): m/z 367 (M)$^+$. IR (NaCl) v (cm$^{-1}$): 3394, 2931, 2839, 1635, 1466, 1250, 1068. $^1$H NMR (CDCl$_3$, 360 MHz) δ (ppm): 0.81-0.95 (m, 3H), 1.53-1.83 (m, 3H), 1.86-1.96 (m, 1H), 2.53-3.01 (m, 4H) 3.19 (m, 2H), 3.66 (s, 2H), 3.78 (s, 3H), 3.80 (s, 3H), 4.02 (m, 1H), 6.61-6.72 (m, 2H), 6.80-6.90 (m, 2H) 7.04-7.24 (m, 3H). $^{13}$C NMR (CDCl$_3$, 90 MHz) δ (ppm): 11.5, 11.7, 22.7, 24.8, 26.8, 27.5, 28.0, 28.1, 29.7, 29.9, 40.5, 41.0, 43.9, 46.5, 51.7, 53.4, 54.5, 55.2, 55.3, 106.9, 107.0, 114.1, 120.8, 120.9, 123.7, 124.4, 126.2, 126.6, 127.7, 129.5, 129.8, 136.5, 137.0, 157.3, 157.4, 158.4, 158.4, 170.9, 171.3.
CHN (%): C$_{23}$H$_{29}$NO$_3$; calculated (×0.3 H$_2$O): C, 74.08; H, 8.00; N, 3.76. found: C, 74.20 H, 8.40; N, 3.65.

N-(8-Methoxytetralin-2-yl)-N-propyl-2-(2,5-dimethylphenyl)acetamide (A4-4: R=OMe, Cy=2,5-dimethylphenyl)

A mixture of 340 mg (2.1 mmol) 2,5-dimethylphenylacetic acid (A3-4: W=OH, Cy=2,5-dimethylphenyl) and 0.70 mL diisopropylethylamine (DIPEA) (4.24. mmol) in 10 mL of dry DMF was cooled in an ice-bath. After addition of 950 mg (2.5 mmol) O-(7-azabenzotriazol-1-yl)-1,1,3,3-tetramethyluronium hexafluorophosphate (HATU) in 5.0 mL dry DMF a solution of 640 mg (2.9 mmol) of the free base of N-(8-methoxytetralin-2-yl)-N-propylamine (A2-1) in 8.0 mL dry DMF was added dropwise, the ice-bath was removed and the reaction mixture was stirred for 3 hrs at room temperature. The mixture was washed with a saturated solution of aqueous NaHCO$_3$ for several times and the resulting aqueous layer was extracted with CH$_2$Cl$_2$. The organic layers were dried over MgSO$_4$ and the solvent was evaporated in vacuo. Flash chromatography of the residue on silica gel with a mixture of hexane/ethyl acetate 60/10 gave the product N-(8-methoxytetralin-2-yl)-N-propyl-2-(2,5-dimethylphenyl)acetamide.

Yield: 660 mg of a light-yellow solid (88%).
MP: 96° C.
MS (EIMS): m/z 365 (M)$^+$. IR (NaCl) v (cm$^{-1}$): 3386, 2927, 2866, 1643, 1466, 1254, 1068. $^1$H NMR (CDCl$_3$, 360 MHz) δ (ppm): 0.90 (t, J=7.4 Hz, 3H), 1.61-1.99 (m, 4H), 2.19 (s, 3H), 2.26 (s, 3H), 2.58-3.37 (m, 6H), 3.61-3.72 (m, 2H), 3.80 (s, 3H), 3.95 (m, 1H), 6.62-6.72 (m, 2H), 6.91-7.13 (m, 4H). $^{13}$C NMR (CDCl$_3$, 90 MHz) δ (ppm): 11.5, 11.7, 19.2, 19.3, 20.9, 20.9, 22.8, 24.8, 26.9, 27.5, 28.0, 28.3, 29.8, 29.9, 38.9, 39.3, 44.0, 46.7, 51.8, 54.4, 55.2, 107.0, 107.0, 120.8, 120.8, 123.7, 124.4, 126.2, 126.6, 127.4, 127.5, 129.6, 129.7, 130.1, 130.1, 133.0, 133.2, 134.0, 134.0, 135.4, 135.5, 136.5, 137.0, 157.4, 157.4, 170.7, 171.1.
CHN (%): C$_{24}$H$_{31}$NO$_2$; calculated: C, 78.87; H, 8.55; N, 3.83. found: C, 78.82; H, 8.67; N, 3.85.

N-(8-Methoxytetralin-2-yl)-N-propyl-2-(2-biphenyl-4-yl)acetamide (A4-5: R=OMe, Cy=2-biphenyl-4-yl)

Synthesis worked according to the preparation of A4-4 when using 370 mg (1.7 mmol) N-(8-methoxytetralin-2-yl)-N-propylamine (A2-1: R=OMe) and 250 mg (1.2 mmol) 2-biphenyl-4-acetic acid (A3-5: W=OH, Cy=2-biphenyl-4-yl). Flash chromatography of the residue on silica gel with a mixture of hexane/ethyl acetate 20/1 gave the product.

Yield: 469 mg of a white solid (97%).
MP: 43° C.
MS (EIMS): m/z 413 (M)$^+$. IR (NaCl) v (cm$^{-1}$): 2962, 2933, 2837, 1635, 1583, 1466, 1444, 1254, 1115, 1092, 756. $^1$H NMR (CDCl$_3$, 360 MHz) δ (ppm): 0.85-0.97 (m, 3H), 1.57-1.86 (m, 3H), 1.94 (m, 1H), 2.56-3.04 (m, 4H), 3.23 (m, 2H), 3.76-3.82 (m, 5H), 4.06 (m, 1H), 6.63-6.72 (m, 2H), 7.09 (dd, J=7.8 Hz, 7.7 Hz, 1H), 7.29-7.46 (m, 5H), 7.51-7.62 (m, 4H). $^{13}$C NMR (CDCl$_3$, 150 MHz) δ (ppm): 11.5, 11.7, 22.7, 24.9, 26.9, 27.5, 28.0, 28.2, 29.8, 29.9, 41.0, 41.5, 44.0, 46.6, 51.8, 54.6, 55.2, 107.0, 107.0, 120.8, 120.8, 123.6, 124.4, 126.2, 126.6, 127.0, 127.1, 127.2, 127.2, 127.3, 127.4, 128.7, 129.0, 129.3, 134.7, 134.8, 136.5, 137.0), 139.6, 139.6, 140.8, 141.0, 157.4, 157.4, 170.5, 170.9.
CHN (%): C$_{28}$H$_{31}$NO$_2$; calculated: C, 81.32; H, 7.56; N, 3.39. found: C, 81.42; H, 7.33; N, 3.43.

N-(8-Methoxytetralin-2-yl)-N-propyl-2-adamantylacetamide (A4-6: R=OMe, Cy=adamantyl)

Synthesis worked according to the preparation of A4-4 when using 570 mg (2.6 mmol) N-(8-methoxytetralin-2-yl)-N-propylamine (A2-1: R=OMe) and 360 mg (1.9 mmol) 2-adamantylacetic acid (A3-6: W=OH, Cy=adamantyl). Flash chromatography of the residue on silica gel with a mixture of hexane/ethyl acetate 10/1 gave the product.

Yield: 580 mg of colourless oil (78%).
MS (EIMS): m/z 395 (M)$^+$. IR (NaCl) v (cm$^{-1}$): 3421, 2900, 2846, 1631, 1466, 1254, 1095, 756. $^1$H NMR (CDCl$_3$, 360 MHz) δ (ppm): 0.85-0.94 (m, 3H), 1.51-1.76 (m, 15H), 1.82-2.02 (m, 4H), 2.04-2.31 (m, 2H), 2.59 (m, 1H), 2.81-2.99 (m, 3H), 3.19 (m, 2H), 3.80 (s, 3H), 4.10 (m, 1H), 6.62-6.77 (m, 2H), 7.04-7.17 (m, 1H). $^{13}$C NMR (CDCl$_3$, 150 MHz) δ (ppm): 11.5, 11.8, 23.2, 24.9, 27.1, 27.8, 28.2, 28.4, 28.8, 28.8, 29.9, 29.9, 33.5, 33.8, 36.8, 36.9, 42.8, 42.9, 43.7, 46.5, 46.6, 46.7, 50.7, 54.8, 55.3, 106.9, 107.0, 120.8, 120.8, 123.9, 124.5, 126.2, 126.6, 136.6, 137.1, 157.4, 157.4, 170.7, 171.4.

CHN (%): $C_{26}H_{37}NO_2$; calculated: C, 78.94; H, 9.43; N, 3.54. found: C, 78.77; H, 9.71; N, 3.36.

2c. Synthesis of Amines According to Formula A5

Compounds according to formula A4 were hydrogenized using reductive agents like lithium aluminiumhydride in diethyl ether. The reaction was terminated by adding an aqueous solution of sodium hydrogen carbonate, the mixture was purified over Celite™, the amine was extracted with organic solvents and purified by flash chromatography to get derivatives of formula A5 which represent final compounds as embodiments of this disclosure

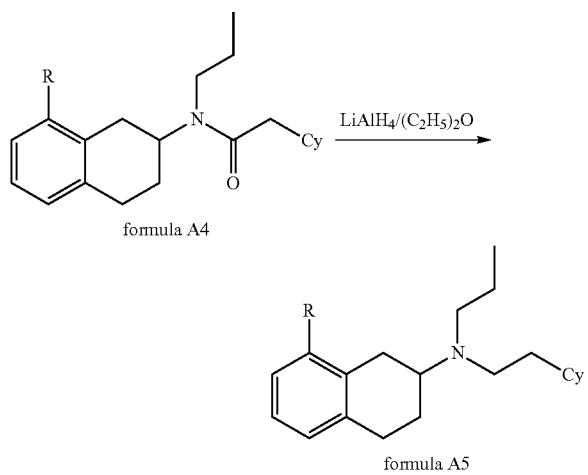

Compound 2: N-(8-Methoxytetralin-2-yl)-N-propyl-N-[2-(2-thienyl)ethyl]amine (A5-1: R=OMe, Cy=2-thienyl)

To a solution of 16 mg (0.05 mmol) of N-(8-methoxytetralin-2-yl)-N-propyl-2-(2-thienyl)acetamide (A4-1: R=OMe, Cy=2-thienyl) in 10 mL dry diethyl ether 0.15 mL of a 1 M solution of LiAlH$_4$ (0.15 mmol) in dry diethyl ether were added dropwise and stirred for 20 hrs at room temperature. The reaction was terminated by adding a saturated aqueous solution of sodium hydrogen carbonate, the solution was filtered through a matrix consisting of Celite™ —MgSO$_4$—Celite™ and subsequently washed with methylenchloride and ethyl acetate. After evaporating the organic solvents in vacuo the residue was purified by flash chromatography on silica gel with a mixture of hexane/ethyl acetate 10/1 in the presence of 0.5% (v/v) dimethylethylamine to get compound (N-(8-methoxytetralin-2-yl)-N-propyl-N-[2-(2-thienyl)ethyl]amine (A5-1: R=OMe, Cy=2-thienyl)).

Yield: 9.8 g of colorless oil (64%).
MS (EIMS): m/z 329 (M)$^+$. IR (NaCl) v (cm$^{-1}$): 3356, 2927, 1585, 1466, 1435, 1254, 1072, 1022. $^1$H NMR (CDCl$_3$, 360 MHz) δ (ppm): 0.90 (t, J=7.3 Hz, 3H), 1.50 (m, 2H), 1.55-1.67 (m, 1H), 1.99 (m, 1H), 2.43 (dd, J=18.2 Hz, 12.2 Hz, 1H), 2.57 (m, 2H), 2.76-3.03 (m, 8H), 3.81 (s, 3H), 6.65 (d, J=8.1 Hz, 1H), 6.70 (m, 1H), 6.81 (m, 1H), 6.91 (dd, J=5.2 Hz, 3.4 Hz, 1H), 7.07 (dd, J=7.9 Hz, 5.2 Hz, 1H), 7.11 (dd, J=5.2 Hz, 1.2 Hz, 1H). $^{13}$C NMR (CDCl$_3$, 90 MHz) δ (ppm): 11.9, 22.5, 25.5, 26.2, 30.2, 30.3, 52.8, 52.9, 55.2, 57.2, 106.8, 120.8, 123.1, 124.4, 125.4, 126.0, 126.5, 137.9, 143.3, 157.6.
CHN (%): $C_{20}H_{27}NOS$; calculated: C, 72.90; H, 8.26; N, 4.25 S, 9.73. found: C, 72.69; H, 8.25; N, 4.13; S, 9.39.

Compound 2a: (R)—N-(8-Methoxytetralin-2-yl)-N-propyl-N-[2-(2-thienyl)ethyl]amine ((R)-A5-1: R=OMe, Cy=2-thienyl)

Synthesis worked according to the preparation of A5-1 when using 45 mg (0.13 mmol) (R)—N-(8-methoxytetralin-2-yl)-N-propyl-2-(2-thienyl)acetamide ((R)-A4-1: R=OMe, Cy=2-thienyl). Flash chromatography was done using a mixture of hexane/ethyl acetate 40/1 in the presence of 0.5% (v/v) dimethylethylamine.

Yield: 25 mg of colorless oil (57%).
MS, IR, $^1$H NMR and $^{13}$C NMR are identical with the data of compound A5-1.
$[\alpha]_D^{27}$=+59.8° (in MeOH).

Compound 2b: (S)—N-(8-Methoxytetralin-2-yl)-N-propyl-N-[2-(2-thienyl)ethyl]amine ((S)-A5-1: R=OMe, Cy=2-thienyl)

Synthesis worked according to the preparation of A5-1 when using 340 mg (0.99 mmol) (S)—N-(8-methoxytetralin-2-yl)-N-propyl-2-(2-thienyl)acetamide ((S)-A4-1: R=OMe, Cy=2-thienyl). Flash chromatography was done using a mixture of hexane/ethyl acetate 40/1 in the presence of 0.5% (v/v) dimethylethylamine.

Yield: 73 mg of colorless oil (23%).
MS, IR, $^1$H NMR and $^{13}$C NMR are identical with the data of compound A5-1.
$[\alpha]_D^{27}$=−56.3° (in MeOH).

Compound 4: N-(8-Methoxytetralin-2-yl)-N-(2-phenylethyl)-N-propylamine (A5-2: R=OMe, Cy=phenyl)

Synthesis worked according to the preparation of A5-1 when using 120 mg (0.37 mmol) N-(8-methoxytetralin-2-yl)-N-propyl-2-phenylacetamide (A4-2: R=OMe, Cy=phenyl). Flash chromatography was done using a mixture of hexane/ethyl acetate 20/1 in the presence of 0.5% (v/v) dimethylethylamine.

Yield: 88 mg of a light yellow oil (74%).
MS (EIMS): m/z 323 (M)$^+$. IR (NaCl) v (cm$^{-1}$): 3381, 2933, 1468, 1255, 1070, 769. $^1$H NMR (CDCl$_3$, 360 MHz) δ (ppm): 0.90 (t, J=7.4 Hz, 3H), 1.51 (m, 2H), 1.56-1.67 (m, 1H), 1.98 (m, 1H), 2.43 (m, 1H), 2.57 (m, 2H), 2.72-3.04 (m, 8H), 3.81 (s, 1H), 6.65 (d, J=8.1 Hz, 1H), 6.69 (d, J=7.6 Hz, 1H), 7.07 (dd, J=8.1 Hz, 7.6 Hz, 1H), 7.14-7.30 (m, 5H). $^{13}$C NMR (CDCl$_3$, 90 MHz) δ (ppm): 11.9, 22.4, 25.5, 26.2, 30.2, 36.2, 52.8, 53.1, 55.2, 57.1, 106.8, 120.8, 125.4, 125.8, 125.9, 128.2, 128.8, 137.9, 141.0, 157.6.
CHN (%): $C_{22}H_{29}NO$; calculated (×0.2 H$_2$O): C, 80.79; H, 9.06; N, 4.28. found: C, 80.69; H, 9.17; N, 4.24.

Compound 6: N-[2-(4-Methoxyphenyl)ethyl]-N-(8-methoxytetralin-2-yl)-N-propylamine (A5-3: R=OMe, Cy=4-methoxyphenyl)

Synthesis worked according to the preparation of A5-1 when using 140 mg (0.39 mmol) N-(8-methoxytetralin-2-yl)-N-propyl-2-(4-methoxyphenyl)acetamide (A4-3: R=OMe, Cy=4-methoxyphenyl). Flash chromatography was done using a mixture of hexane/ethyl acetate 20/1 in the presence of 0.5% (v/v) dimethylethylamine.

Yield: 110 mg of a light yellow oil (77%).
MS (EIMS): m/z 353 (M)$^+$. IR (NaCl) v (cm$^{-1}$): 3392, 2935, 1468, 1252, 1034, 771. $^1$H NMR (CDCl$_3$, 360 MHz) δ (ppm): 0.90 (t, J=7.4 Hz, 3H), 1.50 (m, 2H, 1.55-1.67 (m, 1H, 1.98 (m, 1H, 2.42 (dd, J=18.2 Hz, 12.6 Hz, 1H), 2.57 (m, 2H), 2.67-3.03 (m, 8H), 3.78 (s, 3H), 3.81 (s, 3H), 6.65 (d, J=8.1 Hz, 1H), 6.69 (d, J=7.7 Hz, 1H), 6.82 (m, 2H), 7.07 (dd, J=8.1 Hz, 7.7 Hz, 1H), 7.12 (m, 2H). $^{13}$C NMR (CDCl$_3$, 150 MHz) δ (ppm): 11.9, 22.4, 25.5, 26.2, 30.2, 35.3, 52.8, 53.3, 55.2, 55.2, 57.1, 106.8, 113.7, 120.8, 125.4, 125.9, 129.7, 133.1, 137.9, 157.6, 157.8.

CHN (%): C$_{23}$H$_{31}$NO$_2$; calculated (×0.125 H$_2$O): C, 77.65; H, 8.85; N, 3.94. found: C, 77.55; H, 9.03; N, 3.89.

Compound 8: N-(8-Methoxytetralin-2-yl)-N-propyl-N-[2-(2,5-dimethyl)phenylethyl]amine (A5-4: R=OMe, Cy=2,5 dimethylphenyl)

Synthesis worked according to the preparation of A5-1 when using 510 mg (1.4 mmol) N-(8-methoxytetralin-2-yl)-N-propyl-2-(2,5-dimethyl)phenylacetamide (A4-4: R=OMe, Cy=2,5-dimethylphenyl). Flash chromatography was done using a mixture of hexane/ethyl acetate 20/1 in the presence of 0.5% (v/v) dimethylethylamine.

Yield: 350 mg of a yellow oil (72%).

MS (EIMS): m/z 351 (M)$^+$. IR (NaCl) v (cm$^{-1}$): 3417, 2931, 1647, 1466, 1254, 1068. $^1$H NMR (CDCl$_3$, 360 MHz) δ (ppm): 0.92 (t, J=7.4 Hz, 3H), 1.48-1.68 (m, 3H), 2.02 (m, 1H), 2.29 (s, 6H), 2.44 (dd, J=18.2 Hz, 12.2 Hz, 1H), 2.60 (m, 2H), 2.67-3.06 (m, 8H), 3.81 (s, 3H), 6.65 (d, J=8.1 Hz, 1H), 6.70 (m, 1H), 6.90 (dd, J=7.6 Hz, 1.9 Hz, 1H), 6.96 (d, J=1.9 Hz, 1H), 7.01 (d, J=7.6 Hz, 1H), 7.07 (dd, J=8.1 Hz, 7.7 Hz, 1H). $^{13}$C NMR (CDCl$_3$, 90 MHz) δ (ppm): 11.9, 18.9, 20.9, 22.2, 25.6, 26.2, 30.2, 33.5, 51.7, 52.9, 55.2, 57.3, 106.9, 120.8, 125.3, 126.0, 126.7, 130.1, 130.2, 132.8, 135.3, 137.8, 138.7, 157.6.

CHN (%): C$_{24}$H$_{33}$NO; calculated (×0.2 H$_2$O): C, 81.17; H, 9.48; N, 3.94. found: C, 81.30; H, 9.48; N, 3.94.

Compound 10: N-(2-Adamantylethyl)-N-(8-methoxytetralin-2-yl)-N-propylamine (A5-5: R=OMe, Cy=adamantyl)

Synthesis worked according to the preparation of A5-1 when using 560 mg (1.4 mmol) N-(8-methoxytetralin-2-yl)-N-propyl-2-adamantylacetamide (A4-5: R=OMe, Cy=adamantyl). Flash chromatography was done using a mixture of hexane/ethyl acetate 30/1 in the presence of 0.5% (v/v) dimethylethylamine.

Yield: 340 mg of a light yellow oil (63%).

MS (EIMS): m/z 381 (M)$^+$. IR (NaCl) v (cm$^{-1}$): 3379, 2900, 2843, 1585, 1466, 1254, 1072. $^1$H NMR (CDCl$_3$, 360 MHz) δ (ppm): 0.89 (t, J=7.4 Hz, 3H), 1.27 (m, 2H), 1.42-1.74 (m, 15H), 1.88-2.02 (m, 4H), 2.36-2.99 (m, 9H), 3.82 (s, 3H), 6.65 (d, J=8.0 Hz, 1H), 6.70 (m, 1H), 7.07 (dd, J=8.0 Hz, 7.8 Hz, 1H). $^{13}$C NMR (CDCl$_3$, 90 MHz) δ (ppm): 12.0, 22.2, 25.3, 26.2, 28.8, 30.2, 32.1, 37.3, 42.6, 44.5, 52.9, 55.3, 54.1, 106.9, 120.8, 125.4, 126.0, 137.9, 157.6.

CHN (%): C$_{26}$H$_{39}$NO; calculated (×0.4 H$_2$O): C, 80.32; H, 10.32; N, 3.60. found: C, 80.18; H, 10.28; N, 3.59.

N-[2-(2-Biphenyl-4-yl)ethyl]-N-(8-methoxytetralin-2-yl)-N-propylamine (A5-6: R=OMe, Cy=2-biphenyl-4-yl)

Synthesis worked according to the preparation of A5-1 when using 470 mg (1.1 mmol) N-(8-methoxytetralin-2-yl)-N-propyl-2-(2-biphenyl-4-yl)acetamide (A4-5: R=OMe, Cy=2-biphenyl-4-yl) and THF as the solvent. Flash chromatography was done using hexane in the presence of 0.5% (v/v) dimethylethylamine.

Yield: 210 mg of a light yellow oil (47%).

MS (EIMS): m/z 399 (M)$^+$. IR (NaCl) v (cm$^{-1}$): 3417, 3006, 2930, 2870, 2835, 1585, 1468, 1438, 1339, 1252, 1097, 1072, 1008, 763, 697. $^1$H NMR (CDCl$_3$, 360 MHz) δ (ppm): 0.91 (t, J=7.4 Hz, 3H), 1.47-1.68 (m, 3H), 2.00 (m, 1H), 2.44 (m, 1H), 2.59 (m, 2H), 2.76-3.05 (m, 8H), 3.81 (s, 3H), 6.65 (d, J=8.1 Hz, 1H), 6.70 (d, J=7.6 Hz, 1H), 7.07 (dd, J=8.1 Hz, 7.6 Hz, 1H), 7.26-7.34 (m, 3H), 7.42 (m, 2H), 7.48-7.61 (m, 4H). $^{13}$C NMR (CD$_3$OD, 90 MHz) δ (ppm): 11.9, 22.4, 25.6, 26.2, 30.2, 35.9, 52.8, 53.0, 55.2, 57.2, 106.8, 120.8, 125.4, 126.0, 126.9, 127.0, 128.7, 129.2, 137.9, 138.8, 140.1, 141.2, 157.6.

CHN (%): C$_{28}$H$_{33}$NO; calculated: C, 84.17; H, 8.32; N, 3.51. found: C, 84.31; H, 8.29; N, 3.66.

Compound 12: N-(2-Ferrocenylethyl)-N-(8-methoxytetralin-2-yl)-N-propylamine (A5-7: R=OMe, Cy=ferrocenyl)

Synthesis worked according to the preparation of A4-4 when using 360 mg (1.6 mmol) N-(8-methoxytetralin-2-yl)-N-propylamine (A2-1: R=OMe) and 240 mg (0.99 mmol) ferrocenylacetic acid (A3-7: W=OH, Cy=ferrocenyl). Flash chromatography of the residue on silica gel with a mixture of hexane/ethyl acetate 10/1 gave the crude product N-(8-methoxytetralin-2-yl)-N-propyl-2-ferrocenylacetamide.

Because of its instability the residue was immediately reacted to get compound 12 (N-(2-ferrocenylethyl)-N-(8-methoxytetralin-2-yl)-N-propylamine (A5-7: R=OMe, Cy=ferrocenyl)). This reaction was achieved according to the preparation of A5-1 when using 98 mg of crude N-(8-methoxytetralin-2-yl)-N-propyl-2-ferrocenylacetamide dissolved in a mixture of 5.0 mL diethyl ether and 3.0 mL THF. Flash chromatography was done using a mixture of hexane/ethyl acetate 40/1 in the presence of 0.5% (v/v) dimethylethylamine to yield compound 12.

Yield: 25 mg of a yellow oil (6%).

MS (EIMS): m/z 431 (M)$^+$. IR (NaCl) v (cm$^{-1}$): 3774, 3329, 2819, 1815, 1664, 1589, 1406, 1203, 1057, 1026, 783. $^1$H NMR (CDCl$_3$, 360 MHz) δ (ppm): 0.91 (t, J=7.4 Hz, 3H), 1.51 (m, 2H), 1.62 (m, 1H), 1.99 (m, 1H), 2.38-2.58 (m, 5H), 2.69-3.02 (m, 6H), 3.81 (s, 3H), 4.02-4.12 (m, 9H), 6.65 (m, 1H), 6.70 (m, 1H), 7.07 (dd, J=8.0 Hz, 7.7 Hz, 1H). $^{13}$C NMR (CDCl$_3$, 150 MHz) δ (ppm): 12.0, 22.4, 25.6, 26.2, 29.5, 30.2, 52.1, 52.8, 55.2, 57.0, 67.1, 67.1, 68.1, 68.4, 87.2, 106.8, 120.8, 125.4, 126.0, 137.9, 157.6.

HR-MS: C$_{26}$H$_{33}$FeNO; calculated: 431.1912. found: 431.1912.

Compound 14: N-(8-Methoxytetralin-2-yl)-N-propyl-N-[2-([2.2]paracyclophan-4-yl)ethyl]-amine (A5-8: R=OMe, Cy=[2.2]paracyclophan-4-yl)

Synthesis worked according to the preparation of A4-4 when using 160 mg (0.75 mmol) N-(8-methoxytetralin-2-yl)-N-propylamine (A2-1: R=OMe) and 110 mg (0.42 mmol) [2.2]paracyclophan-4-ylacetic acid (A3-8: W=OH, Cy=[2.2]paracyclophan-4-yl). Flash chromatography of the residue on silica gel with a mixture of hexane/ethyl acetate 40/10 gave the crude product N-(8-methoxytetralin-2-yl)-N-propyl-2-([2.2]paracyclophan-4-yl)acetamide. The residue was dissolved in 5.0 mL diethyl ether and reacted as described for the preparation of A5-1. Flash chromatography was done using a mixture of hexane/ethyl acetate 20/1 in the presence of 0.5% (v/v) dimethylethylamine to yield compound 14.

Yield: 58 mg of a light yellow oil (31%).

MS (EIMS): m/z 453 (M)⁺. IR (NaCl) ν (cm⁻¹): 3418, 2929, 2853, 1666, 1586, 1469, 1438, 1254, 1096, 1070, 796, 767, 716. ¹H NMR (CDCl₃, 360 MHz) δ (ppm): 0.93 (m, 3H), 1.48-1.68 (m, 3H, Pr-2), 2.00 (m, 1H), 2.34-3.17 (m, 18H), 3.37 (m, 1H), 3.81 (s, 3H), 6.14 (m, 1H), 6.36-6.54 (m, 5H), 6.63-6.73 (m, 3H), 7.08 (dd, J=8.1 Hu, 7.8 Hz, 1H). ¹³C NMR (CDCl₃, 150 MHz) δ (ppm): 12.0, 22.4, 25.6, 25.8, 26.1, 26.2, 30.1, 30.2, 30.2, 33.6, 34.3, 35.0, 35.3, 51.9, 52.0, 53.0, 53.1, 55.2, 57.3, 57.3, 106.8, 120.7, 120.8, 125.4, 126.0, 129.1, 130.4, 132.1, 133.1, 133.3, 134.6, 134.7, 135.0, 135.1, 137.5, 137.6, 137.9, 139.3, 139.4, 139.6, 139.7, 140.0, 140.1, 157.6.

2d. Synthesis of Amines According to Formula A7

Compounds according to formula I carrying a hydroxyl group at position 8 (R=OH) and being identical to the general structure as described in formula A7 were synthesized starting from compounds according to formula A6 (R1=(C1-C3)alkyl), which have already been synthesized as embodiments of this disclosure. Acid supported hydrolysis of the methoxy group of compounds according to formula A6 (R1=Me) was achieved by utilizing borotribromide (Horn Pharmaceutisch Weekblad Sci. Ed. 1985, Vol 7, p 208) as a Lewis acid in methylenchloride to afford the 8-OH substituted final compounds according to formula A7 as embodiments of this disclosure.

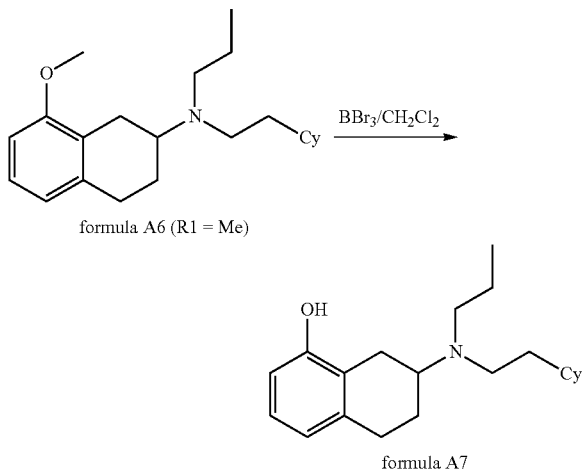

formula A6 (R1 = Me)

formula A7

Compound 1: N-(8-Hydroxytetralin-2-yl)-N-propyl-N-[2-(2-thienyl)ethyl]amine (A7-1: R=OMe, Cy=2-thienyl)

A solution of 6.5 g (20 mmol) of N-(8-methoxytetralin-2-yl)-N-propyl-N-[2-(2-thienyl)ethyl]amine (A5-1: R=OMe, Cy=2-thienyl) in 40 mL dry methylenchoride was added to a solution of 80 mL of a 1M solution of BBr₃ in methylenchloride (80 mmol) and was stirred for 3 hrs at room temperature. The reaction solution was added to a mixture of 5.0 mL 25% aqueous NH₃ and 15 g ice and further stirred for 45 min. The organic and the aqueous phase were separated and the last one was extracted with methylenchloride for several times. All organic phases were collected, washes with saturated aqueous solutions of sodium hydrogen carbonate and sodium chloride, respectively and dried over MgSO₄. The solvent was evaporated in vacuo and the residue was purified by flash chromatography using a mixture of hexane/ethyl acetate 10/1 in the presence of 1% (v/v) of dimethylethylamine.

Yield: 1.1 g of a light brown solid (17%).
MP: 99° C.
MS (EIMS): m/z 315 (M)⁺. IR (NaCl) ν (cm⁻¹): 3367, 2931, 2870, 1585, 1462, 1261, 1080. ¹H NMR (CDCl₃, 600 MHz) δ (ppm): 0.91 (t, J=7.4 Hz, 3H, —CH₂—CH₂—CH₃), 1.46-1.66 (m, 3H, —CH₂—CH₂—CH₃, axial H-3'), 2.01 (m, 1H, equatorial H-3'), 2.42 (dd, J=16.3 Hz, 11.2 Hz, 1H, axial H-1'), 2.58 (m, 2H, —CH₂—CH₂—CH₃), 2.75-3.07 (m, 8H, equatorial H-1', H-2', axial H-4', equatorial H-4', N—CH₂—CH₂-thienyl, N—CH₂—CH₂-thienyl), 6.60 (m, 1H, H-7'), 6.68 (m, 1H, H-5'), 6.82 (m, 1H, H-3), 6.92 (dd, J=5.2 Hz, 3.4 Hz, 1H, H-4), 6.98 (m, 1H, H-6'), 7.12 (dd, J=5.2 Hz, 1.2 Hz, 1H, H-5). ¹³C NMR (CD₃OD, 150 MHz) δ (ppm): 11.9 (—CH₂—CH₂—CH₃), 22.4 (—CH₂—CH₂—CH₃), 25.5 (C-1' or C-3'), 25.6 (C-3' or C-1'), 30.2 (C-4' or N—CH₂—CH₂-thienyl), 30.3 (N—CH₂—CH₂-thienyl or C-4'), 52.7 (—CH₂—CH₂—CH₃ or N—CH₂—CH₂-thienyl), 52.9 (N—CH₂—CH₂-thienyl or —CH₂—CH₂—CH₃), 57.2 (C-2'), 111.9 (C-7'), 121.0 (C-5'), 122.9 (C-8a'), 123.2 (C-5), 124.6 (C-3), 126.3 (C-6'), 126.6 (C-4), 138.2 (C-4a'), 143.3 (C-2), 153.7 (C-8').
CHN (%): C₁₉H₂₅NOS; calculated (×0.125 H₂O): C, 71.83; H, 8.01; N, 4.41; S, 10.09. found: C, 71.90; H, 8.25; N, 4.32; S, 10.11.

Compound 1a: (R)—N-(8-Hydroxytetralin-2-yl)-N-propyl-N-[2-(2-thienyl)ethyl]amine ((R)-A7-1: Cy=2-thienyl)

Synthesis worked according to the preparation of A7-1 when using 21 mg (0.06 mmol) (R)—N-(8-methoxytetralin-2-yl)-N-propyl-N-[2-(2-thienyl)ethyl]amine ((R)-A5-1: R=OMe, Cy=2-thienyl). Flash chromatography was done using hexane/ethyl acetate 40/10 in the presence of 0.5% (v/v) dimethylethylamine to achieve compound 1a.
Yield: 14 mg of a light yellow oil (70%).
MS, ¹H NMR and ¹³C NMR are identical with the data of compound A7-1.
$[\alpha]_D^{27}$=+47.6° (in MeOH).

Compound 1b: (S)—N-(8-Hydroxytetralin-2-yl)-N-propyl-N-[2-(2-thienyl)ethyl]amine ((S)-A7-1: Cy=2-thienyl)

Synthesis worked according to the preparation of A7-1 when using 76 mg (0.23 mmol) (S)—N-(8-methoxytetralin-2-yl)-N-propyl-N-[2-(2-thienyl)ethyl]amine ((S)-A5-1: R=OMe, Cy=2-thienyl). Flash chromatography was done using hexane/ethyl acetate 10/1 in the presence of 1% (v/v) of dimethylethylamine to achieve compound 1b.
Yield: 39 mg of colorless oil (52%).
MS, ¹H NMR and ¹³C NMR are identical with the data of compound A7-1.
$[\alpha]_D^{22}$=−28.2° (in MeOH).

Compound 3: N-(8-Hydroxytetralin-2-yl)-N-(2-phenylethyl)-N-propylamine (A7-2: Cy=phenyl)

Synthesis worked according to the preparation of A7-1 when using 58 mg (0.18 mmol) N-(8-methoxytetralin-2-yl)-N-(2-phenylethyl)-N-propylamine (A5-2: R=OMe, Cy=phenyl). Flash chromatography was done using hexane/ethyl acetate 40/10 in the presence of 0.5% (v/v) dimethylethylamine to achieve compound 3.
Yield: 32 mg of a yellow oil (57%).
MS (EIMS): m/z 309 (M)⁺. IR (NaCl) ν (cm⁻¹): 3386, 2931, 2870, 1585, 1462, 1331, 1269, 1084, 876. ¹H NMR (CDCl$_3$, 360 MHz) δ (ppm): 0.91 (t, J=7.4 Hz, 3H), 1.46-1.65 (m, 3H), 2.00 (m, 1H), 2.39 (dd, J=16.2 Hz, 11.2 Hz, 1H), 2.59 (m, 2H.), 2.72-3.07 (m, 8H), 6.60 (d, J=7.9 Hz, 1H), 6.67 (d, J=7.5 Hz, 1H), 6.98 (dd, J=7.9 Hz, 7.5 Hz, 1H), 7.16-7.31 (m, 5H). $^{13}$C NMR (CDCl$_3$, 90 MHz) δ (ppm): 11.9, 22.3, 25.6, 30.2, 36.2, 52.8, 52.9, 57.1, 111.9, 120.9, 122.9, 125.9, 126.3, 128.2 128.9, 138.3, 140.9, 153.7.

CHN (%): C$_{21}$H$_{27}$NO; calculated (×0.1 H$_2$O): C, 81.04; H, 8.81; N, 4.50. found: C, 81.36; H, 9.26; N, 4.11.

Compound 5: N-(8-Hydroxytetralin-2-yl)-N-[2-(4-methoxyphenyl)ethyl]-N-propylamine (A7-3: Cy=4-methoxyphenyl)

Synthesis worked according to the preparation of A7-1 when using 80 mg (0.23 mmol) N-(8-methoxytetralin-2-yl)-N-[2-(4-methoxyphenyl)ethyl]-N-propylamine (A5-3: R=OMe, Cy=4-methoxyphenyl). Flash chromatography was done using hexane/ethyl acetate 30/20 in the presence of 0.5% (v/v) dimethylethylamine to achieve compound 5.

Yield: 46 mg light yellow oil (60%).

MS (EIMS): m/z 325 (M)$^+$. IR (NaCl) ν (cm$^{-1}$): 3394, 2920, 2862, 1639, 1439, 1045, 663. $^1$H NMR (CD$_3$OD, 360 MHz) δ (ppm): 0.94 (t, J=7.4 Hz, 3H), 1.51-1.64 (m, 3H), 2.05 (m, 1H), 2.45 (dd, J=17.7 Hz, 12.6 Hz, 1H), 2.60-3.06 (m, 10H), 6.54 (s, 1H), 6.56 (s, 1H), 6.70 (m, 2H), 6.88 (dd, J=8.0 Hz, 7.7 Hz, 1H), 7.03 (m, 2H). $^{13}$C NMR (CD$_3$OD, 90 MHz) δ (ppm): 12.2, 22.5, 26.9, 27.0, 30.9, 35.0, 53.9, 54.4, 58.9, 112.6, 116.2, 120.7, 124.0, 127.1, 130.6, 132.5, 138.8, 156.3, 156.7.

Compound 7: N-[2-(2,5-Dimethylphenyl)ethyl]-N-(8-hydroxytetralin-2-yl)-N-propylamine (A7-4: Cy=2,5-dimethylphenyl)

Synthesis worked according to the preparation of A7-1 when using 63 mg (0.18 mmol) N-[2-(2,5-dimethylphenyl)ethyl]-N-(8-methoxytetralin-2-yl)-N-propylamine (A5-4: R=OMe, Cy=2,5-dimethylphenyl). Flash chromatography was done using hexane/ethyl acetate 40/10 in the presence of 0.5% (v/v) dimethylethylamine to achieve compound 7.

Yield: 47 mg of a white solid (79%).

MP: 102° C.

MS (EIMS): m/z 337 (M)$^+$. IR (NaCl) ν (cm$^{-1}$): 3383, 2931, 2873, 1647, 1585, 1462, 1041. $^1$H NMR (CDCl$_3$, 600 MHz) δ (ppm): 0.93 (t, J=7.3 Hz, 3H), 1.52-1.65 (m, 3H), 2.04 (m, 1H), 2.29 (s, 6H), 2.42 (dd, J=16.1 Hz, 11.3 Hz, 1H), 2.61 (m, 2H.), 2.69-2.92 (m, 7H), 3.05 (m, 1H), 6.60 (d, J=7.8 Hz, 1H), 6.68 (d, J=7.6 Hz, 1H), 6.92 (dd, J=7.8 Hz, 1.8 Hz, 1H), 6.96 (d, J=1.8 Hz, 1H), 6.99 (d, J=7.8 Hz, 1H), 7.02 (dd, J=7.8 Hz, 7.6 Hz, 1H). $^{13}$C NMR (CDCl$_3$, 90 MHz) δ (ppm): 12.0, 18.9, 20.9, 22.3, 25.7, 25.7, 30.2, 33.7, 51.6, 53.0, 57.2, 111.9, 120.9, 122.9, 126.3, 126.7, 130.1, 130.3, 132.8, 135.3, 137.3, 138.7, 153.7.

CHN (%): C$_{25}$H$_{37}$NO; calculated (×0.2 H$_2$O): C, 80.99; H, 9.28; N, 4.11. found: C, 80.97; H, 8.33; N, 4.05.

Compound 9: N-(2-Adamantylethyl)-N-(8-hydroxytetralin-2-yl)-N-propylamine (A7-5: Cy=adamantyl)

Synthesis worked according to the preparation of A7-1 when using 78 mg (0.20 mmol) N-(2-adamantylethyl)-N-(8-methoxytetralin-2-yl)-N-propylamine (A5-5: R=OMe, Cy=adamantyl). Flash chromatography was done using hexane/ethyl acetate 40/10 in the presence of 0.5% (v/v) dimethylethylamine to achieve compound 9.

Yield: 56 mg of a colorless oil (74%).

MS (EIMS): m/z 367 (M)$^+$. IR (NaCl) ν (cm$^{-1}$): 3394, 2900, 2846, 1643, 1585, 1462, 1045. $^1$H NMR (CDCl$_3$, 600 MHz) δ (ppm): 0.89 (t, J=7.4 Hz, 3H), 1.27 (m, 2H), 1.46-1.54 (m, 8H), 1.56-1.72 (m, 7H), 1.93 (m, 3H), 2.01 (m, 1H), 2.44-2.52 (m, 3H), 2.57 (m, 2H), 2.78-2.91 (m, 3H), 3.00 (m, 1H), 6.60 (d, J=7.9 Hz, 1H), 6.65 (d, J=7.7 Hz, 1H), 6.98 (dd, J=7.9 Hz, 7.7 Hz, 1H). $^{13}$C NMR (CDCl$_3$, 150 MHz) δ (ppm): 12.0, 22.3, 25.4, 25.8, 28.7, 30.2, 32.0, 37.2, 42.6, 44.5, 52.8, 57.0, 111.9, 120.9, 123.1, 126.2, 138.4, 153.8.

CHN (%): C$_{25}$H$_{37}$NO; calculated: C, 81.69; H, 10.15; N, 3.81. found: C, 81.62; H, 10.55; N, 3.35.

N-[2-(2-Biphenyl-4-yl)ethyl]-N-(8-hydroxytetralin-2-yl)-N-propylamine (A7-6: Cy=2-biphenyl-4-yl)

Synthesis worked according to the preparation of A7-1 when using 120 mg (0.29 mmol) N-[2-(2-biphenyl-4-yl)ethyl]-N-(8-methoxytetralin-2-yl)-N-propylamine (A5-6: R=OMe, Cy=2-biphenyl-4-yl). Flash chromatography was done using hexane/ethyl acetate 40/10 in the presence of 1% (v/v) dimethylethylamine to achieve compound A7-6.

Yield: 39 mg of a white solid (35%).

MP: 52° C.

MS (EIMS): m/z 385 (M)$^+$. IR (NaCl) ν (cm$^{-1}$): 3388, 2957, 2931, 2870, 1585, 1486, 1464, 1331, 1266, 1085, 825, 763, 732, 697. $^1$H NMR (CDCl$_3$, 360 MHz) δ (ppm): 0.92 (t, J=7.4 Hz, 3H), 1.47-1.68 (m, 3H), 2.02 (m, 1H), 2.45 (dd, J=16.1 Hz, 11.1 Hz, 1H), 2.60 (m, 2H), 2.75-2.93 (m, 7H), 3.05 (m, 1H), 6.59 (d, J=7.7 Hz, 1H), 6.68 (d, J=7.5 Hz, 1H), 6.98 (dd, J=7.7 Hz, 7.5 Hz, 1H), 7.25-7.35 (m, 3H), 7.42 (m, 2H), 7.51 (m, 2H), 7.57 (m, 2H). $^{13}$C NMR (CDCl$_3$, 90 MHz) δ (ppm): 11.9, 22.3, 25.6, 25.8, 30.2, 35.8, 52.9, 52.9, 57.1, 111.9, 120.9, 123.0, 126.2, 127.0, 128.7, 129.3, 138.3, 138.9, 140.0, 141.1, 153.7.

Compound 11: N-(2-Ferrocenylethyl)-N-(8-hydroxytetralin-2-yl)-N-propylamine (A7-7: Cy=ferrocenyl)

Synthesis worked according to the preparation of A7-1 when using 73 mg (0.17 mmol) N-(2-ferrocenylethyl)-N-(8-methoxytetralin-2-yl)-N-propylamine (A5-7: R=OMe, Cy=ferrocenyl). Flash chromatography was done using hexane/ethyl acetate 30/20 in the presence of 0.5% (v/v) dimethylethylamine to achieve compound 11.

Yield: 31 mg of a red brown oil (43%).

MS (EIMS): m/z 417 (M)$^+$. IR (NaCl) ν (cm$^{-1}$): 3398, 2927, 2854, 1589, 1462, 1435, 1053. $^1$H NMR (CDCl$_3$/CD$_3$OD, 360 MHz) δ (ppm): 0.95 (t, J=7.4 Hz, 3H), 1.49-1.70 (m, 3H), 2.07 (m, 1H), 2.44-2.58 (m, 3H), 2.61 (m, 2H), 2.75-3.08 (m, 6H), 4.01-4.10 (m, 4H), 4.12 (s, 5H), 6.61 (m, 1H), 6.63 (m, 1H), 6.95 (dd, J=7.9 Hz, 7.7 Hz, 1H). $^{13}$C NMR (CDCl$_3$, 90 MHz) δ (ppm): 11.2, 20.9, 24.8, 25.6, 27.7, 29.5, 51.4, 52.4, 56.9, 66.7, 67.5, 67.9, 86.1, 111.9, 119.2, 122.5, 125.6, 137.2, 154.5.

CHN (%): C$_{25}$H$_{31}$FeNO; calculated (×0.5 H$_2$O): C, 70.42; H, 7.56; N, 3.29. found: C, 70.35; H, 7.50; N, 3.36.

Compound 13: N-(8-Hydroxytetralin-2-yl)-N-[2-([2.2]paracyclophan-4-yl)ethyl]-N-propylamine (A7-8: Cy=[2.2]paracyclophan-4-yl)

Synthesis worked according to the preparation of A7-1 when using 34 mg (0.07 mmol) N-(8-methoxytetralin-2-yl)-N-[2-([2.2]paracyclophan-4-yl)ethyl]-N-propylamine (A5-8: R=OMe, Cy=[2.2]paracyclophan-4-yl). Flash chromatography was done using hexane/ethyl acetate 40/10 in the presence of 1% (v/v) dimethylethylamine to achieve compound 13.

Yield: 22 mg of colorless oil (65%).

MS (EIMS): m/z 440 (M)$^+$. IR (NaCl) ν (cm$^{-1}$): 3359, 3033, 2929, 2852, 1586, 1464, 1436, 1331, 1265, 1085, 768, 737, 716. $^1$H NMR (CDCl$_3$, 360 MHz) δ (ppm): 0.94 (t, J=7.3 Hz, 3H), 1.49-1.64 (m, 3H), 2.01 (m, 1H), 2.31-3.16 (m, 18H), 3.36 (m, 2H), 6.13 (m, 1H), 6.37-6.52 (m, 5H), 6.59 (d, J=7.9 Hz, 1H), 6.64-6.69 (m, 2H), 6.98 (t, J=8.0 Hz, 7.7 Hz, 1H). $^{13}$C NMR (CDCl$_3$, 150 MHz) δ (ppm): 12.0, 22.2, 25.5, 25.5, 25.6, 25.7, 30.1 30.2, 33.6, 33.7, 34.3, 35.0, 35.3, 51.8, 51.9, 53.1, 53.2, 57.2, 57.3, 111.9, 120.7, 120.8, 123.0, 126.2, 129.1, 130.4, 130.5, 132.1, 132.2, 133.1, 133.3, 134.6, 134.7, 135.1, 135.4, 137.5, 137.7, 138.1, 138.2, 139.3, 139.4, 139.5, 139.7, 140.0, 140.1, 153.8.

2e. Synthesis of Further Exemplary Compounds

The synthesis of exemplary compounds according to formula I can be achieved under the reaction conditions as described above (Chapter 2a to 2d).

N-(8-Methoxytetralin-2-yl)-N-propyl-N-[2-(3-thienyl)ethyl]amine (A5-9: R=OMe, Cy=3-thienyl)

Synthesis works according to the preparation of A4-1 or A4-4 when using N-(8-methoxytetralin-2-yl)-N-propylamine (A2-1: R=OMe) and 3-thienyl acetic acid (A3-9: Cy=3-thienyl) (purchasable from Sigma-Aldrich, Munich (Germany); order number: 220639) and subsequent reaction according to the synthesis of A5-1.

N-(8-Hydroxytetralin-2-yl)-N-propyl-N-[2-(3-thienyl)ethyl]amine (A7-9: Cy=3-thienyl)

Synthesis works according to the preparation of A7-1 when using N-(8-methoxytetralin-2-yl)-N-propyl-N-[2-(3-thienyl)ethyl]amine (A5-9: R=OMe, Cy=3-thienyl).

N-(2-Benzo[b]thienylethyl)-N-(8-methoxytetralin-2-yl)-N-propylamine (A5-10: R=OMe, Cy=2-benzo[b]thienyl)

Synthesis works according to the preparation of A4-1 or A4-4 when using N-(8-methoxytetralin-2-yl)-N-propylamine (A2-1: R=OMe) and 2-benzo[b]thienyl acetic acid (A3-10: R=OMe, Cy=2-benzo[b]thienyl) (purchasable from Rare Chemicals, Kiel (Germany); order number: GT HW 0344) and subsequent reaction according to the synthesis of A5-1.

N-(2-Benzo[b]thienylethyl)-N-(8-hydroxytetralin-2-yl)-N-propylamine (A7-10: Cy=2-benzo[b]thienyl)

Synthesis works according to the preparation of A7-1 when using N-(2-benzo[b]thienylethyl)-N-(8-methoxytetralin-2-yl)-N-propylamine (A5-10: R=OMe, Cy=2-benzo[b]thienyl).

N-(3-Benzo[b]thienylethyl)-N-(8-methoxytetralin-2-yl)-N-propylamine (A5-11: R=OMe, Cy=3-benzo[b]thienyl)

Synthesis works according to the preparation of A4-1 or A4-4 when using N-(8-methoxytetralin-2-yl)-N-propylamine (A2-1: R=OMe) and 3-benzo[b]thienyl acetic acid (A3-11: R=OMe, Cy=3-benzo[b]thienyl) (purchasable from Alfa Aesar, Karlsruhe (Germany); order number: LO 5855 or Maybridge, Tintagel, Cornwall (UK); order number: S11080) and subsequent reaction according to the synthesis of A5-1.

N-(3-Benzo[b]thienylethyl)-N-(8-hydroxytetralin-2-yl)-N-propylamine (A7-11: Cy=3-benzo[b]thienyl)

Synthesis works according to the preparation of A7-1 when using N-(3-benzo[b]thienylethyl)-N-(8-methoxytetralin-2-yl)-N-propylamine (A5-11: R=OMe, Cy=3-benzo[b]thienyl).

N-(8-Methoxytetralin-2-yl)-N-propyl-N-(2-pyrazolo[1,5-a]pyridinylethyl)amine (A5-12: R=OMe, Cy=2-pyrazolo[1,5-a]pyridinyl)

Synthesis works according to the preparation of A4-1 or A4-4 when using N-(8-methoxytetralin-2-yl)-N-propylamine (A2-1: R=OMe) and 2-pyrazolo[1,5-a]pyridinyl acetic acid (A3-12: R=OMe, Cy=2-pyrazolo[1,5-a]pyridinyl) (synthesis according to literature: Awano, K. Chem Pharm Bull 1992, Vol 40, p 631; Löber, S Bioorg Med Chem Lett 2002, Vol 12, p 2377) and subsequent reaction according to the synthesis of A5-1.

N-(8-Hydroxytetralin-2-yl)-N-propyl-N-(2-pyrazolo[1,5-a]pyridinylethyl)amine (A7-12: Cy=2-pyrazolo[1,5-a]pyridinyl)

Synthesis works according to the preparation of A7-1 when using N-(8-methoxytetralin-2-yl)-N-propyl-N-(2-pyrazolo[1,5-a]pyridinylethyl)amine (A5-12: R=OMe, Cy=2-pyrazolo[1,5-a]pyridinyl).

N-(8-Methoxytetralin-2-yl)-N-propyl-N-(3-pyrazolo[1,5-a]pyridinylethyl)amine (A5-13: R=OMe, Cy=3-pyrazolo[1,5-a]pyridinyl)

Synthesis works according to the preparation of A4-1 or A4-4 when using N-(8-methoxytetralin-2-yl)-N-propylamine (A2-1: R=OMe) and 3-pyrazolo[1,5-a]pyridinyl acetic acid (A3-13: R=OMe, Cy=3-pyrazolo[1,5-a]pyridinyl) (synthesis according to literature: Gmeiner, P. Arch Pharm 1988, Vol 321, p 517) and subsequent reaction according to the synthesis of A5-1.

N-(8-Hydroxytetralin-2-yl)-N-propyl-N-(3-pyrazolo[1,5-a]pyridinylethyl)amine (A7-13: Cy=3-pyrazolo[1,5-a]pyridinyl)

Synthesis works according to the preparation of A7-1 when using N-(8-methoxytetralin-2-yl)-N-propyl-N-(3-pyrazolo[1,5-a]pyridinylethyl)amine (A5-13: R=OMe, Cy=3-pyrazolo[1,5-a]pyridinyl).

Exemplary compounds according to formula I with R=OR1 and with R1=—C(=O)R2 can be synthesized via reaction of compounds according to formula A7 with appropriate acid derivatives according to formula 8 under the conditions which are common to form an ester bound to get compounds according to formula 8

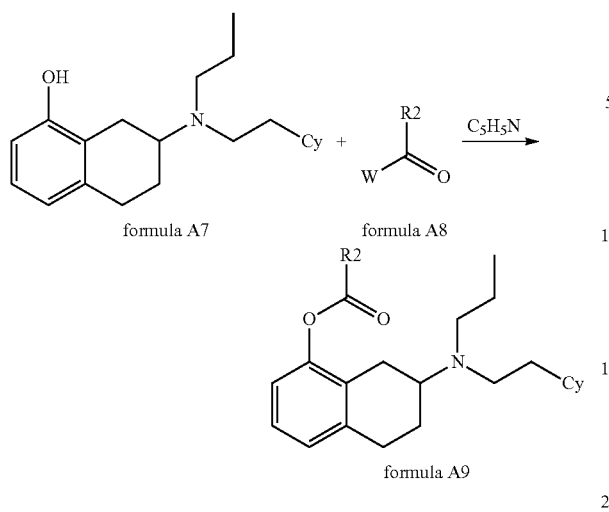

formula A7 + formula A8 →(C5H5N) formula A9

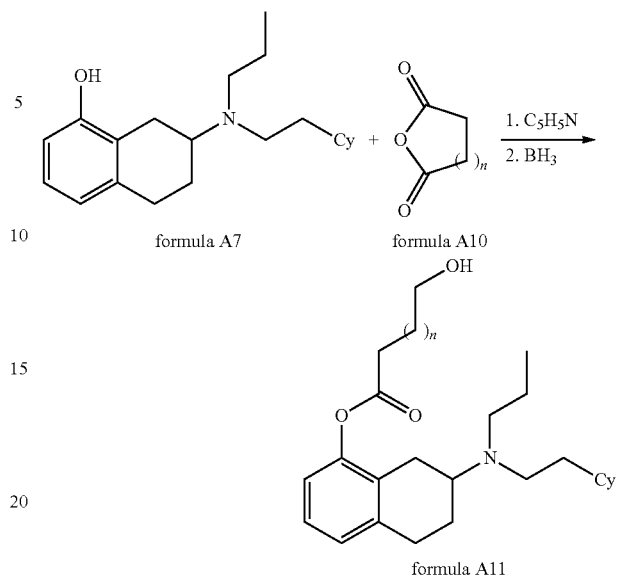

formula A7 + formula A10 →(1. C5H5N, 2. BH3) formula A11 and wherein in anyone of the formulas A7, A8 and A9 the residues R2 and Cy are as defined further above and in the disclosures for compounds of formula I and wherein W is selected of chloro, bromo or alkylcarbonyloxy.

Acetic acid 7-[N-propyl-N-[2-(2-thienyl)ethyl]amino]tetralin-1-yl ester (A9-1:R2=Me, Cy=2-thienyl)

The synthesis of the ester A9-1 works when reacting N-(8-hydroxytetralin-2-yl)-N-propyl-N-[2-(2-thienyl)ethyl]amine (A7-1: Cy=2-thienyl) with acetic acid chloride (A8-1: W=Cl, R2=Me) according to standard conditions to form ester groups for example in pyridine at room temperature for several hours.

Carbonic acid ethyl 7-[N-propyl-N-[2-(2-thienyl)ethyl]amino]tetralin-1-yl ester (A9-2: R2=ethyloxy, Cy=2-thienyl)

The synthesis of the ester A9-2 works when reacting N-(8-hydroxytetralin-2-yl)-N-propyl-N-[2-(2-thienyl)ethyl]amine (A7-1: Cy=2-thienyl) with ethoxycarbonyl chloride (A8-2: W=Cl, R2=ethyloxy) according to standard conditions to form ester groups for example in pyridine at room temperature for several hours.

To synthesize compounds according to formula I with R is equal to a hydroxy substituted (C1-C6)alkylcarbonyloxy group specified by formula A11 (n=1, 2, 3) the approbriate acid derivative may be introduced by utilizing cyclic anhydric acids of different ring seizure according to formula A10 (n=1, 2, 3) to get the ω-substituted carboxy derivatives which can be reduced by complex hydrides like borane (BH3) to achieve compounds according to formula A11 with n=1, 2 or 3 and with Cy being defined as described further above and in the disclosures for compounds of formula I

4-Hydroxybutanoic acid 7-[N-propyl-N-[2-(2-thienyl)ethyl]amino]tetralin-1-yl ester (A11-1: n=1)

Reaction of N-(8-hydroxytetralin-2-yl)-N-propyl-N-[2-(2-thienyl)ethyl]amine (A7-1: Cy=2-thienyl) with succinic acid anhydride (A10-1: n=1) according to standard acylation conditions for example in pyridine at room temperature for several hours yields the appropriate succinic acid mono ester which can be reduced by BH3 to get the 4-hydroxybutanoic acid ester A11-1 (n=2).

5-Hydroxypentanoic acid 7-[N-propyl-N-[2-(2-thienyl)ethyl]amino]tetralin-1-yl ester (A11-2: n=2)

Reaction of N-(8-hydroxytetralin-2-yl)-N-propyl-N-[2-(2-thienyl)ethyl]amine (A7-1: Cy=2-thienyl) with glutaric anhydride (A10-2: n=2) according to standard acylation conditions for example in pyridine at room temperature for several hours yields the appropriate glutaric acid mono ester which can be reduced by BH3 to get the 5-hydroxypentanoic acid ester A11-2 (n=2).

The synthesis of compounds according to formula I with R is equal to S(C1-C3)alkyl specified by formula A12 can be achieved when starting with halogen substituted precursors according to formula A1 (R=Hal) which are derivatized as described above to get compounds according to formula I (R=Hal). Halogen metal exchange utilizing n-butyl lithium and final substitution of the metal atom with alkyl sulfides yield in alkylthio substituted compounds according to formula 12

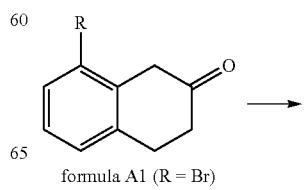

formula A1 (R = Br)

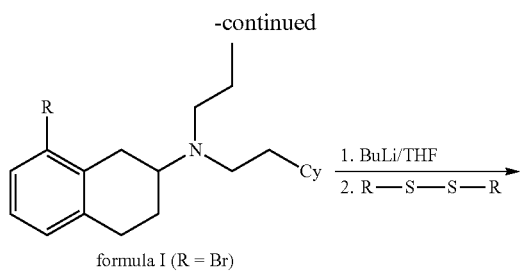

formula I (R = Br)

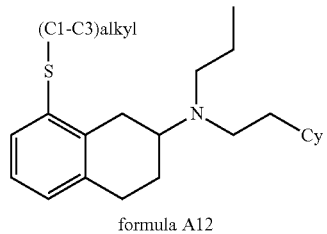

formula A12

N-(8-Methylthiotetralin-2-yl)-N-propyl-N-[2-(3-thienyl)ethyl]amine (A2-1: (C1-C3)alkyl=Me, Cy=2-thienyl)

The precursor 8-bromo-2-tetralone (A1-2: R=Br) (available according to EP0385658) can be reacted as described for A2-1, A4-1 or A4-4 and A5-1 to get N-(8-bromotetralin-2-yl)-N-propyl-N-[2-(3-thienyl)ethyl]amine according to formula I (R=Br, Cy=2-thienyl). Halogen metal exchange in THF using n-butyl lithium results in the 8-lithiated derivative which is reacted with dimethyldisulfide to yield A12-1.

The preparation of compounds bearing a nitrogene in position 8 of the tetraline scaffold according to formula I (R=di(C1-C3)alkylamino or NHR3) starts from the precursor 8-nitro-2-tetralone (A1-3). Reductive amination as described for A2-1 and subsequent amidation using acid derivatives according to formula 3 lead to amids as displayed in formula A4-7. Reduction of the amide group with complex hydrids like lithium aluminium hydride results in the formation of the tertiary amine and the reduction of the nitro to the amino group in position 8 of the compounds according to formula 13.

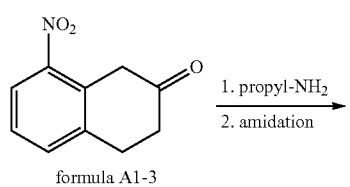

formula A1-3

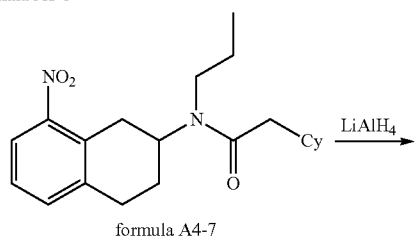

formula A4-7

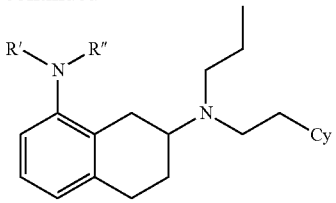

formula A-13

N-(8-Aminotetralin-2-yl)-N-propyl-N-[2-(3-thienyl)ethyl]amine (A13-1: R'=R"=H, Cy=2-thienyl)

Synthesis works according to the preparation of A2-1 starting from 8-nitro-2-tetralone (A1-3) (purchasable from Anichem, North Brunswick, N.J.; order number: N10122 or from Accel Pharmtech, East Brunswick, N.J.; order number: C1061). Amidation according to the preparation of A4-1 or A4-4 gives the intermediate A4-7 (Cy=2-thienyl) with can be reduced with LiAlH$_4$ in diethyl ether to get N-(8-aminotetralin-2-yl)-N-propyl-N-[2-(3-thienyl)ethyl]amine (A13-1: R'=R"=H, Cy=2-thienyl).

N-(8-Methylaminotetralin-2-yl)-N-propyl-N-[2-(3-thienyl)ethyl]amine (A13-2: R'=Me, R"=H, Cy=2-thienyl)

Reductive amination of N-(8-aminotetralin-2-yl)-N-propyl-N-[2-(3-thienyl)ethyl]amine (A13-1: R'=R"=H, Cy=2-thienyl) with stoichiometrically equal amounts of propylamine in the presence of NaBH$_3$CN or NaBH(OAc)$_3$ gives the monomethylamine N-(8-methylaminotetralin-2-yl)-N-propyl-N-[2-(3-thienyl)ethyl]amine (A13-2: R'=Me, R"=H, Cy=2-thienyl).

N-(8-Dimethylaminotetralin-2-yl)-N-propyl-N-[2-(3-thienyl)ethyl]amine (A13-3: R'=R"=Me, Cy=2-thienyl)

Reductive amination of N-(8-aminotetralin-2-yl)-N-propyl-N-[2-(3-thienyl)ethyl]amine (A13-1: R'=R"=H, Cy=2-thienyl) with an excess of propylamine and NaBH$_3$CN or NaBH(OAc)$_3$ gives the dimethylamine derivative N-(8-dimethylaminotetralin-2-yl)-N-propyl-N-[2-(3-thienyl)ethyl]amine (A13-3: R'=R"=Me, Cy=2-thienyl).

7-[N-propyl-N-[2-(2-thienyl)ethyl]amino]tetralin-1-yl formamide (A13-4: R'=formyl, R"=H, Cy=2-thienyl)

Aminolysis of the primary amine N-(8-aminotetralin-2-yl)-N-propyl-N-[2-(3-thienyl)ethyl]amine (A13-1: R'=R"=H, Cy=2-thienyl) with formic acid ethyl ester under the common conditions of an amide formation achieves 7-[N-propyl-N-[2-(2-thienyl)ethyl]amino]tetralin-1-yl formamide (A13-4: R'=formyl, R"=H, Cy=2-thienyl).

7-[N-propyl-N-[2-(2-thienyl)ethyl]amino]tetralin-1-yl carbamic acid ethyl ester (A13-5: R'=ethyloxycarbonyl, R"=H, Cy=2-thienyl)

Aminolysis of the primary amine N-(8-aminotetralin-2-yl)-N-propyl-N-[2-(3-thienyl)ethyl]amine (A13-1: R'=R"=H, Cy=2-thienyl) with ethoxycarbonyl chloride in the presence of pyridine gives 7-[N-propyl-N-[2-(2-thienyl)

ethyl]amino]tetralin-1-yl carbamic acid ethyl ester (A13-5: R'=ethyloxycarbonyl, R"=H, Cy=2-thienyl).

B. Biological Experiments

1) Receptor Binding Assays

Receptor binding data were determined when performing competition binding assays with membrane preparations of cloned cells (stably transfected Chinese Hamster Ovary cells (CHO)) expressing the human receptors and the following radioligands: [$^3$H]spiperone at the human dopamine receptor subtypes hD2$_{long}$, hD2$_{short}$, D3, and hD4.4. Furthermore, membrane homogenates prepared from porcine striatal or cortical tissue were established together with specific radioligands to investigate the following receptors: [$^3$H]SCH 23390 at the porcine striatal pD1 dopamine receptor, [$^3$H]WAY100635 at the porcine cortical p5-HT1a and [$^3$H]ketanserin at the porcine cortical p5-HT2 serotonin receptor as well as [$^3$H]prazosin at the porcine cortical pα1 and [$^3$H]RX821002 at the porcine cortical pα2 adrenergic receptor (Huebner, H J Med Chem 2000, Vol 43, p. 756, Schlotter, K J Med Chem 2005, Vol 48, p. 3696).

The results are displayed in Table 1.

Selectivity ratios were calculated by division of the K$_i$ values of the various compounds at the respective receptors through the K$_i$ values at the 5HT1a receptor. Results are displayed in Table 2.

Compounds of formula I and II disclosed herein, specifically those wherein Cy is a 5 or 6 membered aromatic or heteroaromatic ring, for example those which are selected from the group of phenyl, thienyl, furanyl, imidazolyl, 1,2,3-triazolyl, 1,2,4-triazolyl, pyrazolyl, pyridyl, pyrimidyl, which ring maybe unsubstituted or substituted with one or two groups R4, as further defined herein, show excellent affinity to the 5-HT1a receptor and remarkable selectivity over dopaminergic and adrenergic receptors. A particular high selectivity is displayed by those compounds wherein R is a polar group such as e.g. hydroxyl, and/or if Cy is thienyl or phenyl. Table 2a shows a comparison of the compounds of formula II with a free hydroxyl group with the comparative compound 8-OH-DPAT.

Those compounds of the present invention wherein Cy is a bicyclic ring system Y or adamantyl tend to have a better binding to dopaminergic D2, D3 and/or D4 receptors being expressed in lower nanomolar K$_i$ values and may in some instances serve as combined dopamine/serotonin receptor agonist (see Table 2b).

In addition, representative compounds have been shown to be full agonists at the 5-HT1a receptor with EC$_{50}$ values in the low nanomolar range (see Table 3 and Chapter b) Functional assays).

TABLE 1

Receptor binding data of the compounds 1-14 and the reference 8-OH-DPAT at the dopamine, serotonin and adrenergic receptors (K$_i$, values in [nM] as means of 2-8 individual experiments each done as triplicate)

| compound | p5-HT1a | p5-HT2 | pD1 | hD2$_{long}$ | hD2$_{short}$ | hD3 | hD4.4 | pα1 | pα2 |
|---|---|---|---|---|---|---|---|---|---|
| 1 | 0.73 | 3 600 | 9 400 | 260 | 260 | 190 | 190 | 170 | 68 |
| 2 | 2.9 | 12 000 | 6 700 | 160 | 390 | 57 | 390 | 200 | n.d. |
| 1a | 0.52 | 2 500 | 8 800 | 240 | 260 | 100 | 100 | 640 | 56 |
| 2a | 7.3 | 6 000 | 5 200 | 750 | 840 | 230 | 880 | 140 | 64 |
| 1b | 1.8 | 5 500 | 5 400 | 520 | 290 | 49 | 690 | 200 | n.d. |
| 2b | 6.7 | 3 900 | 3 300 | 85 | 58 | 32 | 760 | 140 | n.d. |
| 3 | 0.62 | 5 800 | 9 100 | 760 | 170 | 190 | 590 | 140 | n.d. |
| 4 | 2.5 | 4 200 | 7 300 | 330 | 230 | 51 | 530 | 190 | 60 |
| 5 | 1.1 | 6 600 | 6 200 | 340 | 86 | 95 | 570 | 87 | n.d. |
| 6 | 5.5 | 4 900 | 9 500 | 340 | 260 | 110 | 470 | 230 | n.d. |
| 7 | 1.7 | 1 700 | 2 400 | 140 | 90 | 130 | 490 | 78 | n.d. |
| 8 | 24 | 4 400 | 6 200 | 300 | 180 | 110 | 940 | 510 | n.d. |
| 9 | 3.5 | 1 600 | 2 600 | 16 | 12 | 39 | 350 | 570 | n.d. |
| 10 | 65 | 14 000 | 12 000 | 380 | 190 | 260 | 1 800 | 4 900 | n.d. |
| 11 | 0.32 | 930 | 3100 | 34 | 16 | 52 | 7.4 | 170 | n.d. |
| 12 | 1.8 | 2 200 | 2600 | 38 | 17 | 11 | 3.5 | 92 | n.d. |
| 13 | 15 | 2 100 | 3 500 | 990 | 640 | 170 | 87 | 930 | n.d. |
| 14 | 50 | 7 300 | 1 900 | 48 | 35 | 33 | 110 | 280 | n.d. |
| R-(+)-8-OH-DPAT | 1.2 | 2 100 | 3 300 | 140 | 100 | 43 | 210 | 250 | n.d. |

(n.d. = not determined)

TABLE 2

Receptor binding and selectivity data for compounds 1-14 and the reference 8-OH-DPAT: 5-HT1a receptor vs dopamine, 5-HT2 serotonin and α1 adrenergic receptors; for each compound K$_i$ values [nM] (upper row) and selectivity ratios derived from the equation (ratio = K$_i$ for p5-HT1a/K$_i$ for the respective receptor) (lower row) are listed

| compound | p5-HT1a | Selectivity | pD1 | hD2$_{long}$ | hD2$_{short}$ | hD3 | hD4.4 | p5-HT2 | pα1 |
|---|---|---|---|---|---|---|---|---|---|
| Table 2a: Selective 5-HT1a agonists | | | | | | | | | |
| R-(+)-8-OH-DPAT | 1.2 | K$_i$ [nM] | 3 300 | 140 | 100 | 43 | 210 | 2 100 | 250 |
| | 1 | ratio | 2 800 | 120 | 83 | 36 | 180 | 1 800 | 210 |
| 1 | 0.73 | K$_i$ [nM] | 9 400 | 260 | 260 | 190 | 190 | 3 600 | 170 |
| | 1 | ratio | 13 000 | 360 | 360 | 260 | 260 | 4 900 | 230 |

TABLE 2-continued

Receptor binding and selectivity data for compounds 1-14 and the reference 8-OH-DPAT: 5-HT1a receptor vs dopamine, 5-HT2 serotonin and α1 adrenergic receptors; for each compound $K_i$ values [nM] (upper row) and selectivity ratios derived from the equation (ratio = $K_i$ for p5-HT1a/$K_i$ for the respective receptor) (lower row) are listed

| compound | p5-HT1a | Selectivity | pD1 | hD2$_{long}$ | hD2$_{short}$ | hD3 | hD4.4 | p5-HT2 | pα1 |
|---|---|---|---|---|---|---|---|---|---|
| 1a | 0.52 | $K_i$ [nM] | 8 800 | 240 | 260 | 100 | 100 | 2 500 | 640 |
|  | 1 | ratio | 17 000 | 460 | 500 | 190 | 190 | 4 800 | 1 200 |
| 1b | 1.8 | $K_i$ [nM] | 5 400 | 520 | 290 | 49 | 690 | 5 500 | 200 |
|  | 1 | ratio | 3 000 | 290 | 160 | 26 | 380 | 3 100 | 110 |
| 3 | 0.62 | $K_i$ [nM] | 9 100 | 760 | 170 | 190 | 590 | 5 800 | 140 |
|  | 1 | ratio | 15 000 | 1 200 | 270 | 310 | 950 | 9 400 | 230 |
| 5 | 1.1 | $K_i$ [nM] | 6 200 | 340 | 86 | 95 | 570 | 6 600 | 87 |
|  | 1 | ratio | 5 600 | 310 | 80 | 86 | 520 | 6 000 | 79 |
| 7 | 1.7 | $K_i$ [nM] | 2 400 | 140 | 90 | 130 | 490 | 1 700 | 78 |
|  | 1 | ratio | 1 400 | 82 | 53 | 76 | 290 | 1 000 | 46 |
| Table 2b: Mixed D2/D3/5-HT1a agonists | | | | | | | | | |
| 9 | 3.5 | $K_i$ [nM] | 2 600 | 16 | 12 | 39 | 350 | 1 600 | 570 |
|  | 1 | ratio | 740 | 4.6 | 3.4 | 11 | 100 | 1600 | 160 |
| 10 | 65 | $K_i$ [nM] | 12 000 | 380 | 190 | 260 | 1 800 | 14 000 | 4 900 |
|  | 1 | ratio | 180 | 5.8 | 2.9 | 4.0 | 28 | 220 | 75 |
| 13 | 15 | $K_i$ [nM] | 3 500 | 990 | 640 | 170 | 87 | 2 100 | 930 |
|  | 1 | ratio | 230 | 66 | 43 | 11 | 5.8 | 140 | 62 |
| 14 | 50 | $K_i$ [nM] | 1 900 | 48 | 35 | 33 | 110 | 7 300 | 280 |
|  | 1 | ratio | 38 | 0.96 | 0.70 | 0.66 | 2.2 | 150 | 5.6 |

2) Functional Assays

The 5-HT1a receptor activation was determined in a [$^{35}$S]GTPγS assay as described in literature (Schlotter, K J Med Chem 2005, Vol 48, p 3696). This assay is based on the determination of the binding of the radioactive ligand [$^{35}$S]GTPγS to membranes carrying the proteins for signal transduction of GPCRs. Specific binding of [$^{35}$S]GTPγS is stimulated by activation of the stably expressed human 5-HT1a receptor in a dose-dependent way by agonists for this GPCR and is determined by measuring the radioactive label of the membrane. Non-linear regression analysis of the resulting dose-response curves yields the EC$_{50}$ value in [nM] representing the half maximal concentration which is necessary to activate the receptor completely. Furthermore, the maximal intrinsic activity of the tested compound in [%] can be derived relative to the effect of the reference compound serotonin.

The results of the functional tests of representative compounds of this disclosure are listed in Table 3. Representative curves for the compounds 1 and 2 relative to the reference serotonin (5-HT) are displayed in FIG. 1.

Compound 1 and its (R)-enantiomer 1a show full agonist activity at the human 5-HT1a receptor with a [$^{35}$S]GTPγS incorporation of 103% relative to the effect of serotonin (=100%) and with EC$_{50}$ values of 0.65-1.9 nM being very similar to the $K_i$ values determined in the radioligand displacement experiments for receptor binding. Similar effects were measured for the 8-methoxy derivatives 2 and 2a and the adamantyl substituted compound 9.

TABLE 3

Functional activity at the 5-HT1a receptor determined in a [$^{35}$S]GTPγS assay (mean values of 2-8 individual experiments)

| compound | EC$_{50}$ [nM] | intrinsic activity [% rel. to serotonin] |
|---|---|---|
| serotonin | 3.6 | 100 |
| 1 | 1.9 | 103 |
| 1a | 0.65 | 103 |
| 2 | 6.3 | 91 |

TABLE 3-continued

Functional activity at the 5-HT1a receptor determined in a [$^{35}$S]GTPγS assay (mean values of 2-8 individual experiments)

| compound | EC$_{50}$ [nM] | intrinsic activity [% rel. to serotonin] |
|---|---|---|
| 2a | 1.1 | 82 |
| 9 | 1.9 | 88 |

3) Animal Pain Test (Formalin Assay)

The formalin assay is a chemically induced tonic pain model which indicates a compound's ability to treat pain. The formalin test is being widely accepted as a valid basic model of persistent clinical pain, and may indicate a compound's efficacy in neuropathic and/or inflammatory pain conditions.

Compound 1 and a comparator (gabapentin 100 mg/kg) were administered to groups of 5 or 10 CD-1 (Crl.) derived male mice weighing 24±2 g. Test substances and vehicle (0.2% HPMC/0.9% NaCl) were each administered by intraperitoneal injection (gabapentin) or oral gavage (compound 1) 15 or 30 minutes before subplantar injection of formalin (0.02 ml, 2% solution). Reduction of the formalin-induced hind paw licking time recorded at 5-minute interval during the following 0- to 35-minute after formalin injection by 50 percent or more (≥50%) indicated significant analgesic activity. Also, statistical analysis was performed by using one-way ANOVA followed by Dunnett's test to compare the test compound-treated and vehicle control groups. Significance is considered at P<0.05 level. Acute toxic symptoms and autonomic effects were observed after the administration of test compounds.

Compound 1 showed significant analgesic effect at the 10-20 minutes period after 10 mg/kg oral administration (FIG. 2 and Table 4). While the 3 mg/kg showed some effect, no analgesic effect has been observed after 1 mg/kg administration. Hence, compound 1 dose-dependently demonstrated analgesic effect after oral administration (Table 4).

TABLE 4

Results of the formalin assay after oral administration of compound 1 vs vehicle
Hind Paw Licking Times in Seconds (% Inhibition)

| | observation interval (minutes) | | | | | | |
|---|---|---|---|---|---|---|---|
| | 0-5 | 5-10 | 10-15 | 15-20 | 20-25 | 25-30 | 30-35 |
| vehicle 5 ml/kg | 76.9 ± 7.9 | 2.6 ± 1.5 | 54.5 ± 15 | 100.8 ± 18.6 | 62.4 ± 17.1 | 9.6 ± 4.1 | 14.2 ± 13.3 |
| compound 1 5 mg/kg | 63.4 ± 7.2 (18%) | 10.2 ± 3.9 (0%) | 25.1 ± 11.6 (54%) | 56.7 ± 18 (44%) | 54.7 ± 9.4 (12%) | 54.7 ± 15.1 (0%) | 24.7 ± 9.8 (0%) |
| compound 1 10 mg/kg | 64.3 ± 7.3 (16%) | 0 ± 0 (100%) | 2.0* ± 1.8 (96%) | 31.6* ± 12.3 (69%) | 37.5 ± 13.6 (40%) | 29.9 ± 12.7 (0%) | 12.8 ± 8.8 (10%) |

4) Penetration Through Skin

The in vitro permeation of compound 1 through pig skin from saturated solution (f1) and from a patch (f2) was investigated.

4.1) Pig Skin Permeation from Saturated Solution

For the permeation experiments horizontal cells with an acceptor and donor volume of approx. 23 mL of phosphate buffer pH 6.2 were used. The donor cells contained saturated solutions of compound 1 (2 mg/mL) in phosphate buffer pH 6.2. The experiments were performed at a temperature of 32° C. and the acceptor and donor media were slowly stirred. For the study pig leg skin with thickness of 300-500 μm were used. The experiments were performed in triplicate (n=3) over a period of 48 hours. During this time period six samples at different time points (after 2, 4, 6, 8, 24 and 48 hours) were taken. After each individual incubation period the concentration of the test compound in the acceptor medium was analysed by HPLC at 275 nm, 20° C., flow rate 2.0 mL/min in acetonitrile/water/TFA.

Evaluation: The concentration of the test compound in the acceptor medium was calculated by using an external standard solution with known concentration. Then the concentration of test compound was correlated with the incubation time by linear regression. The flux rate [μg/cm$^2$/h] is equivalent to the slope of the linear equation.

Results: The average flux rate of Compound 1 from saturated solution was determined to be 4.0 μg/cm$^2$/h (mean value of cells 1-3).

4.2) Pig Skin Permeation from Patch

For this permeation experiments Franz diffusion cells with a diffusion area of 2.54 cm$^2$ and an acceptor volume of approx. 100 mL were used. For the study pig leg skin with a thickness of 300-500 μm was used. The permeation experiments were performed at a temperature of 32° C. and the acceptor medium (phosphate buffer pH 6.2) was slowly stirred. A patch of 2.54 cm$^2$ area comprising about 5 wt % of compound 1 in a hydrophobic adhesive layer was fixed on the skin surface. The experiments were performed in triplicate (n=3) over a period of 48 hours. During this time period six samples at different time points (after 2, 4, 6, 8, 24 and 48 hours) were taken. After each individual incubation period the concentration of the test compound in the acceptor medium was analysed by HPLC at 275 nm, 20° C., 2.0 mL/min in acetonitrile/water/TFA.

Results: The average flux rate of Compound 1 from patch was 4.0 μg/cm$^2$/h.

The results of the pig skin permeation experiments are summarized in Table 5.

TABLE 5

Pig skin permeation experiments with compound 1

| | Patch Flux Rate | |
|---|---|---|
| Measured Flux Rate | per cm$^2$/h | 4.01 μg |
| Extrapolated daily flux rate | per 20 cm$^2$ patch/24 hrs | 1.92 mg |
| | per 30 cm$^2$ patch/24 hrs | 2.88 mg |

The flux rate through isolated pig skin both from saturated solution as well as from a drug-in-adhesive patch was identically. The achieved flux rate with a non-optimized patch is already deemed sufficient to deliver a therapeutically effective amount through the skin (e.g. an extrapolated delivery of about 2 mg/24 hrs for a 20 cm$^2$ patch). Further improvement of the flux rate may be possible by optimization of the patch formulation.

C) Physicochemical Characterisation of Compound 1

1) Stability of Compound 1 in PBS Buffer pH 7.4 and SGF with 0.5% DMSO

5 μL DMSO stock solution of compound 1 (2 mg/mL) were diluted with 955 μL PBS buffer pH 7.4 and 995 μL Simulated Gastric Fluid (SGF). After dilution the samples were immediately analysed by HPLC. After the initial injection, each sample solution was repeatedly injected over a period of approximately 12 hours.

Results: No degradation of compound 1 in PBS buffer pH 7.4 and simulated gastric fluid (pH 1-2) over 12 hours at 37° C. was observed.

2) Melting Point

The melting point of compound 1 was determined by DSC. The measurements were performed in perforated pans with a heating rate of 1° C./min. The melting point (Tonset) of compound 1 is about 97.5° C.

3) XRPD Measurements

Crystallinity of the free base of compound 1 was confirmed by Xray diffractogram using Cu k-alpha radiation (lambda=1.540 Å). The main degrees 2 theta peaks (≥5% relative intensity) are depicted in Table 6 and are illustrated in FIG. 3.

TABLE 6

XRPD peaks in degree 2 theta positions (relative intensity in % in brackets)

| XRPD peaks | rel. intensity [%] | XRPD peaks | rel. intensity [%] | XRPD peaks | rel. intensity [%] |
|---|---|---|---|---|---|
| 6.5605 | 37.43 | 11.3713 | 8.60 | 13.1904 | 4.98 |
| 13.2735 | 6.72 | 13.6157 | 6.37 | 15.1796 | 24.11 |

TABLE 6-continued

XRPD peaks in degree 2 theta positions (relative intensity in % in brackets)

| XRPD peaks | rel. intensity [%] | XRPD peaks | rel. intensity [%] | XRPD peaks | rel. intensity [%] |
|---|---|---|---|---|---|
| 15.2668 | 79.16 | 16.3749 | 46.58 | 15.5371 | 9.31 |
| 16.6824 | 100.00 | 17.3662 | 28.74 | 18.5872 | 19.80 |
| 19.8581 | 13.28 | 20.5278 | 16.25 | 20.6209 | 17.00 |
| 21.1673 | 10.72 | 21.4459 | 63.22 | 23.5955 | 58.44 |
| 23.9294 | 23.04 | 24.7873 | 16.07 | 25.1693 | 20.63 |
| 25.5412 | 8.14 | 26.2780 | 5.61 | 26.5836 | 18.85 |
| 27.9429 | 6.90 | 30.3043 | 5.34 | 36.4145 | 8.13 |

The invention claimed is:

1. A compound of formula I

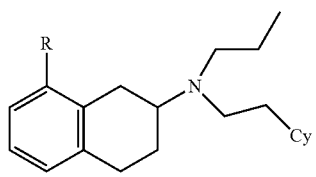

wherein

R is OR1, di(C1-C3)alkylamino, SH, S(C1-C3)alkyl or NHR3;

R1 is hydrogen, a group —C(=O)R2, —SO$_2$CF$_3$, or (C1-C3)alkyl which is unsubstituted or substituted with one or more halogen atoms, R2 is (C1-C6)alkyl, (C1-C6)alkyloxy, phenyl, phenyl(C1-C3)alkyl or phenyl(C1-C3)alkyloxy, wherein the phenyl group is optionally substituted with one or more substituents selected from (C1-C3)alkoxy, (C1-C3)alkyl, halogen, or CF$_3$;

R3 is hydrogen, (C1-C3)alkyl, formyl, (C1-C3)alkylcarbonyl, (C1-C3)alkoxycarbonyl, or (C1-C3)alkylaminocarbonyl;

Cy is an aromatic, heteroaromatic or non-aromatic cyclic group X, Y or Z, wherein X is a 5 membered aromatic or heteroaromatic ring which is unsubstituted or substituted with one or two groups R4, or a 6 membered aromatic or heteroaromatic ring which is substituted with one or two groups R4;

Y is a bicyclic aromatic or heteroaromatic ring system which is unsubstituted or substituted with one to three groups R5 and which ring system is selected from among

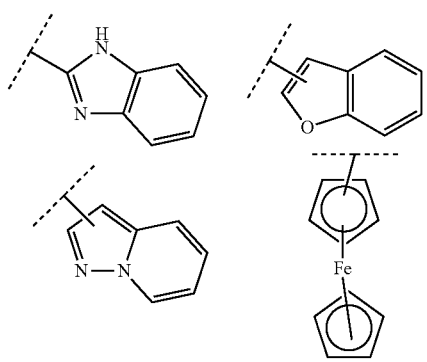

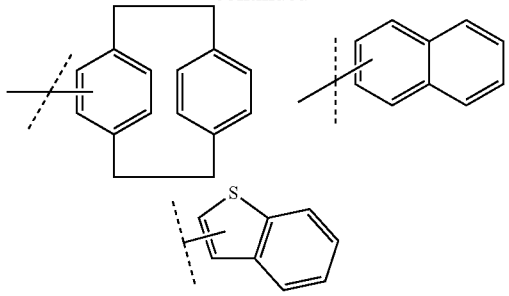

wherein the bond crossed by a dotted line indicates the attachment site of the group Y to the aminotetraline scaffold;

wherein each R4 and R5 is independently selected from halogen, hydroxyl, CF$_3$, (C1-C3)alkyl, or (C1-C3)alkoxy, wherein each alkyl or alkoxy may be substituted with one or more halogens or a hydroxyl group, and Z is adamantyl which is unsubstituted or substituted with methyl and/or hydroxyl including its enantiomers and pharmaceutically acceptable salts.

2. A compound according to claim 1, wherein R is OR1, and R1 is methyl, hydrogen or a group —C(=O)R2 wherein R2 is (C1-C6)alkyl or (C1-C6)alkyloxy.

3. A compound according to claim 1, wherein Cy is a 5 or 6 membered aromatic or heteroaromatic ring which is selected from the group of phenyl, thienyl, furanyl, imidazolyl, 1,2,3-triazolyl, 1,2,4-triazolyl, pyrazolyl, pyridyl, pyrimidyl, and unsubstituted or substituted with one or two groups R4.

4. A compound according to claim 1 and having the general formula II

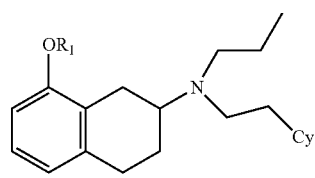

wherein

R1 is hydrogen, a group —C(=O)R2, or (C1-C3)alkyl which is unsubstituted or substituted with one or more halogen atoms, R2 is (C1-C6)alkyl, (C1-C6)alkyloxy, phenyl, phenyl(C1-C3)alkyl or phenyl(C1-C3)alkyloxy, wherein the phenyl group is optionally substituted with one or more substituents selected from (C1-C3)alkoxy, (C1-C3)alkyl, halogen or CF$_3$, Cy is a 5 membered aromatic or heteroaromatic ring selected from the group of phenyl, thienyl, furanyl, each of which is unsubstituted or substituted with one or two groups R4, or a 6 membered aromatic or heteroaromatic ring selected from the group of phenyl, imidazolyl, 1,2,3-triazolyl, 1,2,4-triazolyl, pyrazolyl, pyridyl, pyrimidyl, which is substituted with one or two groups R4, each R4 is independently selected from halogen, (C1-C3)alkyl, or (C1-C3)alkoxy, wherein each alkyl or alkoxy may be substituted with one or more halogens or a hydroxyl group, including its enantiomers and pharmaceutically acceptable salts.

5. A compound according to claim 4, wherein
a. R1 is hydrogen, methyl, or a group —C(=O)R2 wherein R2 is (C1-C6)alkyl or (C1-C6)alkyloxy, and
b. Cy is thienyl which is unsubstituted or substituted with one or two groups R4, which are selected from halogen, hydroxyl, (C1-C3)alkyl, or (C1-C3)alkoxy, wherein each alkyl or alkoxy may be substituted with one or more halogen atoms or a hydroxyl group, or phenyl, which is substituted with one or two groups R4, which are selected from halogen, hydroxyl, (C1-C3)alkyl, or (C1-C3)alkoxy, wherein each alkyl or alkoxy can be substituted with one or more halogen atoms or a hydroxyl group.

6. A compound according to claim 4, wherein
a. R1 is hydrogen or methyl and
b. Cy is phenyl or thienyl, wherein the phenyl is optionally substituted with one or two groups R4 which are independently selected from halogen, hydroxyl, (C1-C3)alkyl, (C1-C3)alkoxy, or $CF_3$.

7. A compound according to claim 1 and selected from
N-(8-Hydroxytetralin-2-yl)-N-propyl-N-[2-(2-thienyl)ethyl]amine
(R)—N-(8-Hydroxytetralin-2-yl)-N-propyl-N-[2-(2-thienyl)ethyl]amine
(S)—N-(8-Hydroxytetralin-2-yl)-N-propyl-N-[2-(2-thienyl)ethyl]amine
N-(8-Methoxytetralin-2-yl)-N-propyl-N-[2-(2-thienyl)ethyl]amine
(R)—N-(8-Methoxytetralin-2-yl)-N-propyl-N-[2-(2-thienyl)ethyl]amine
(S)—N-(8-Methoxytetralin-2-yl)-N-propyl-N-[2-(2-thienyl)ethyl]amine
N-[2-(4-Hydroxyphenyl)ethyl]-N-(8-hydroxytetralin-2-yl)-N-propylamine
N-[2-(4-Methoxyphenyl)ethyl]-N-(8-methoxytetralin-2-yl)-N-propylamine
N-[2-(2,5-Dimethylphenyl)ethyl]-N-(8-hydroxytetralin-2-yl)-N-propylamine
N-[2-(2,5-Dimethylphenyl)ethyl]-N-(8-methoxytetralin-2-yl)-N-propylamine
N-[2-(1-Adamantyl)ethyl]-N-(8-hydroxytetralin-2-yl)-N-propylamine
N-[2-(1-Adamantyl)ethyl]-N-(8-methoxytetralin-2-yl)-N-propylamine
N-(2-Ferrocenylethyl)-N-(8-hydroxytetralin-2-yl)-N-propylamine
N-(2-Ferrocenylethyl)-N-(8-methoxytetralin-2-yl)-N-propylamine,
and pharmaceutically acceptable salts thereof.

8. A compound according to claim 1 further comprising N-(8-Hydroxytetralin-2-yl)-N-propyl-N-[2-(2-thienyl)ethyl]amine or a pharmaceutically acceptable salt thereof.

9. A compound according to claim 1 for use in therapy.

10. A pharmaceutical composition comprising at least one compound according to claim 1 and a pharmaceutically acceptable carrier.

11. Utilizing a compound according to claim 1 for preparing a medicament for the treatment of a disease which is selected from the group of depression, anxiety or panic disorder, attention deficit hyperactivity disorder (ADHD), and pain.

12. A compound according to claim 2, wherein R2 is (C1-C6)alkyl.

13. A compound according to claim 5, wherein R2 is (C1-C3)alkyl.

14. A compound according to claim 1 and selected from
N-(8-Hydroxytetralin-2-yl)-N-propyl-N-[2-(2-thienyl)ethyl]amine
(R)—N-(8-Hydroxytetralin-2-yl)-N-propyl-N-[2-(2-thienyl)ethyl]amine
(S)—N-(8-Hydroxytetralin-2-yl)-N-propyl-N-[2-(2-thienyl)ethyl]amine
N-(8-Methoxytetralin-2-yl)-N-propyl-N-[2-(2-thienyl)ethyl]amine
(R)—N-(8-Methoxytetralin-2-yl)-N-propyl-N-[2-(2-thienyl)ethyl]amine
(S)—N-(8-Methoxytetralin-2-yl)-N-propyl-N-[2-(2-thienyl)ethyl]amine
N-[2-(4-Hydroxyphenyl)ethyl]-N-(8-hydroxytetralin-2-yl)-N-propylamine
N-[2-(4-Methoxyphenyl)ethyl]-N-(8-methoxytetralin-2-yl)-N-propylamine
N-[2-(2,5-Dimethylphenyl)ethyl]-N-(8-hydroxytetralin-2-yl)-N-propylamine
N-[2-(2,5-Dimethylphenyl)ethyl]-N-(8-methoxytetralin-2-yl)-N-propylamine
N-[2-(1-Adamantyl)ethyl]-N-(8-hydroxytetralin-2-yl)-N-propylamine
N-[2-(1-Adamantyl)ethyl]-N-(8-methoxytetralin-2-yl)-N-propylamine
N-(2-Ferrocenylethyl)-N-(8-hydroxytetralin-2-yl)-N-propylamine
N-(2-Ferrocenylethyl)-N-(8-methoxytetralin-2-yl)-N-propylamine,
and pharmaceutically acceptable salts thereof.

15. A pharmaceutical composition comprising at least one compound according to claim 1 and a pharmaceutically acceptable carrier adapted for oral or transdermal administration.

16. A compound according to claim 1 further comprising N-(8-Hydroxytetralin-2-yl)-N-propyl-N-[2-(2-thienyl)ethyl]amine or a pharmaceutically acceptable salt thereof, which is enantiopure in (R) configuration.

* * * * *